(12) United States Patent
Finlay et al.

(10) Patent No.: US 7,300,659 B2
(45) Date of Patent: Nov. 27, 2007

(54) **ENTEROHEMORRHAGIC *ESCHERICHIA COLI* VACCINE**

(75) Inventors: B. Brett Finlay, Richmond (CA); Andrew A. Potter, Saskatchewan (CA)

(73) Assignees: University of Saskatchewan, Saskatoon, Saskatchewan (CA); University of British Columbia, Vancouver, British Columbia (CA)

( * ) Notice: Subject to any disclaimer, the term of this patent is extended or adjusted under 35 U.S.C. 154(b) by 622 days.

(21) Appl. No.: 10/039,760

(22) Filed: Jan. 3, 2002

(65) Prior Publication Data

US 2002/0160020 A1   Oct. 31, 2002

Related U.S. Application Data

(60) Provisional application No. 60/259,818, filed on Jan. 4, 2001.

(51) Int. Cl.
*A61K 39/02* (2006.01)
(52) U.S. Cl. .............................. 424/234.1; 424/184.1; 424/203.1
(58) Field of Classification Search ............. 424/257.1, 424/184.1, 203.1, 234.1
See application file for complete search history.

(56) References Cited

U.S. PATENT DOCUMENTS

| | | | | |
|---|---|---|---|---|
| 5,747,309 A | * | 5/1998 | Allan et al. | 424/93.4 |
| 5,951,988 A | * | 9/1999 | Littel-van den Hurk et al. | 424/278.1 |
| 6,136,554 A | * | 10/2000 | Bochner | 435/34 |

FOREIGN PATENT DOCUMENTS

| | | | |
|---|---|---|---|
| JP | 59020226 | * | 2/1984 |
| WO | 99/24567 | * | 5/1999 |

OTHER PUBLICATIONS

Li et al., Infection and Immunity vol. 68, No. 9, pp. 5090-5095, Sep. 2000.*
Dean-Nystrom (Infection and Immunity, vol. 66, No. 9, pp. 4560-4563, 1998).*
Hunt et al, J. Clin. Pathol., 42:847-852, 1989.*
Kudva, (Diss. Abstr. Int., B 1998, 58(10):5252).*
Kobayashi (JP 59020226, published Feb. 1, 1984; translation attached to original Japanese document).*
Pokric (Periodicum Biologorium 101(4)283-302, 1999).*
Allison (Methods: A Companion to Methods in Enzymology, 19:87-93, 1999).*
Morein et al (Methods: A Companion to Methods in Enzymology, 19(1):94-102, 1999).*
Harlow et al (Antibodies: A Laboratory Manual, Cold Spring Harbor Press, 1988, pp. 96-99).*
Wilson et al (Journal of Food Protection, 60(11):1451-1453, 1997).*
Conlan et al., "Oral immunization of mice with a glycoconjugate vaccine containing the O157 antigen of *Escherichia coli* O157:H7 admixed with cholera toxin fails to elicit protection against subsequent colonization by the pathogen," *CAN J. Microbiol.*, 46:283-290(2000).
Conlan et al., "Parenteral immunization with a glycoconjugate vaccine containing the O157 antigen of *Escherichia coli* O157:H7 elicits a systemic humoral immune response in mice, but fails to prevent colonization by the pathogen," *CAN J. Microbiol.*, 45:279-286(1999).
Conlan et al., "Efficacy of Recombinant Leukotoxin in Protection Against Pneumonic Challenge with Live Pasteurella Haemolytica A," *Infection and Immunity*, 59(2)587-591 (1991).
DeVinney et al., "Enterohemorrhagic *Escherichia coli* O157:H7 Produces Tir, Which Is Translocated to the Host Cell Membrane but Is Not Tyrosine Phosphorylated," *Infect. Immun.*, 67:2389-2398 (1999).
Li et al., "Human Response to *Escherichia coli* O157:H7 Infection: Antibodies to Secreted Virulence Factors," *Infec. Immun.*, 68:5090-5095(2000).
van Drunen Littel-van den Hurk et al., "Protection of cattle from BHV-1 infection by immunization with recombinant glycoprotein gIV," *Vaccine*, 11:25-35(1993).

* cited by examiner

*Primary Examiner*—Patricia A. Duffy
(74) *Attorney, Agent, or Firm*—Woodcock Washburn LLP

(57) ABSTRACT

Compositions and methods for stimulating an immune response against a secreted enterohemorragic *Escherichia coli* (EHEC) antigen are disclosed. The compositions comprise EHEC cell culture supernatants.

80 Claims, 9 Drawing Sheets

ENTEROHEMORRHAGIC *ESCHERICHIA COLI* VACCINE

CROSS-REFERENCE TO RELATED APPLICATION

Figure 1:
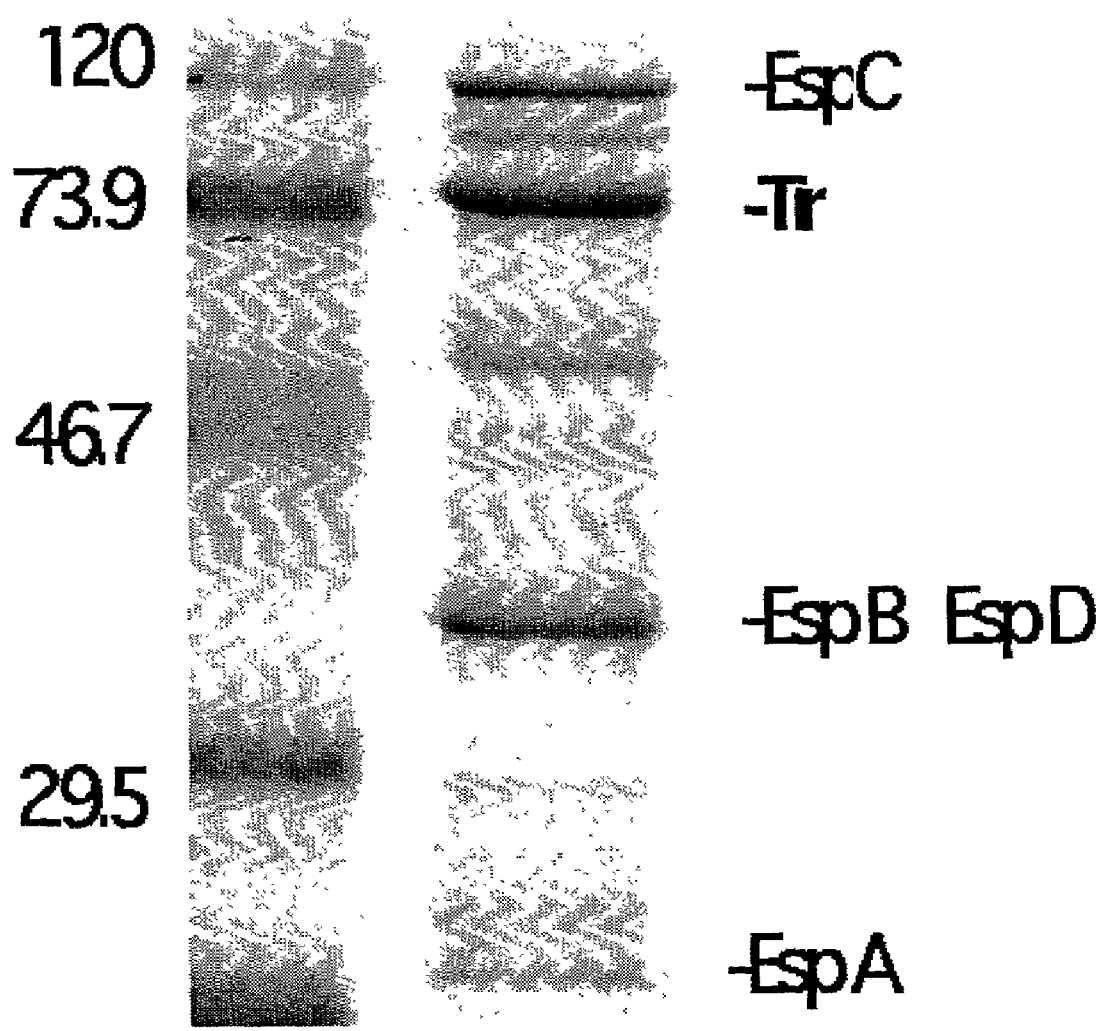

This application claims the benefit under 35 USC §119 (e)(1) of provisional patent application Ser. No. 60/259,818, filed Jan. 4, 2001, which application is incorporated herein by reference in its entirety.

FIELD OF THE INVENTION

The present invention relates to compositions and methods for eliciting an immune response in mammals against enterohemorragic *Escherichia coli*. In particular, the invention relates to the use of cell culture supernatants for treating and preventing enterohemorragic *E. coli* colonization of mammals.

BACKGROUND OF THE INVENTION

Enterohemorragic *Escherichia coli* (EHEC), also called Shiga toxin *E. coli* (STEC) and vertotoxigenic *E. coli* (VTEC) are pathogenic bacteria that cause diarrhea, hemorrhagic colitis, hemolytic uremic syndrome, kidney failure and death in humans. While many Shiga-like toxin-producing EHEC strains are capable of causing disease in humans, those of serotype O157:H7 cause the majority of human illness. This organism is able to colonize the large intestine of humans by a unique mechanism in which a number of virulence determinants are delivered to host cells via a type III secretion system, including the translocated Intimin receptor, Tir (DeVinney et al., *Infect. Immun.* (1999) 67:2389). In particular, these pathogens secrete virulence determinants EspA, EspB and EspD that enable delivery of Tir into intestinal cell membranes. Tir is integrated into the host cell membrane where it serves as the receptor for a bacterial outer membrane protein, Intimin. Tir-Intimin binding attaches EHEC to the intestinal cell surface and triggers actin cytoskeletal rearrangements beneath adherent EHEC that results in pedestal formation. EspA, EspB, Tir and Intimin are each essential for the successful colonization of the intestine by EHEC.

Although EHEC colonize the intestine of ruminants and other mammals, they generally do not cause overt disease in these animals. However, contamination of meat and water by the EHEC serotype O157:H7 (hereinafter, "EHEC O157:H7") is responsible for about 50,000 cases of EHEC O157:H7 infection in humans annually in the United States and Canada that result in approximately 500 deaths. In 1994, the economic cost associated with EHEC O157:H7 infection in humans was estimated to be over 5 billion dollars annually.

The first documented EHEC O157:H7 outbreak traced to contaminated meat occurred in 1982. Subsequently, it was demonstrated that healthy ruminants including, but not limited to, cattle, dairy cows and sheep, could be infected with EHEC O157:H7. In fact, USDA reports indicate that up to 50% of cattle are carriers of EHEC O157:H7 at some time during their lifetime and, therefore, shed EHEC O157:H7 in their feces.

Because of the bulk processing of slaughtered cattle and the low number of EHEC O157:H7 (10–100) necessary to infect a human, EHEC O157:H7 colonization of healthy cattle remains a serious health problem. To address this problem, research has focused on improved methods for detecting and subsequently killing EHEC O157:H7 at slaughter, altering the diet of cattle to reduce the number of intestinal EHEC O157:H7 and immunizing animals to prevent EHEC O157:H7 colonization. Recently, the recombinant production and use of EHEC O157:H7 proteins including recombinant EspA (International Publication No. WO 97/40063), recombinant TIR (International Publication No. WO 99/24576), recombinant EspB and recombinant Intimin (Li et al., Infec. Immun. (2000) 68:5090–5095) have been described. However, production and purification of recombinant proteins in amounts sufficient for use as antigens is both difficult and expensive. At the present time, there is no effective method for blocking EHEC O157:H7 colonization of cattle and other mammals and, thereby, for reducing shedding of EHEC into the environment.

Therefore, there is a need for new compositions and methods for treating and preventing EHEC disease, as well as for reducing EHEC colonization of mammals in order to reduce the incidence of health problems associated with EHEC-contaminated meat and water.

SUMMARY OF THE INVENTION

The present invention satisfies the above need by providing such compositions and methods. In particular, the methods of the present invention make use of a composition comprising a cell culture supernatant (hereinafter "CCS") derived from an EHEC culture to elicit an immune response against one or more EHEC secreted antigens, thereby treating and/or preventing EHEC infection and/or reducing EHEC colonization of the mammal. The compositions can be delivered with or without a coadministered adjuvant. In certain embodiments, EspA and Tir comprise at least 20% of the cell culture supernatant protein. The EHEC culture supernatant may be derived from any EHEC serotype, but is preferably obtained from a culture of EHEC O157:H7 and/or EHEC O157:NM (non-motile). The cell culture supernatant of the present invention is easy and relatively inexpensive to prepare and is effective at dose regimens that have minimal toxicity.

EspA, EspB, Tir and Intimin are necessary for activation (A) of host epithelial cell signal transduction pathways and for the intimate attachment (E) of EHEC to host epithelial cells. Therefore, without being bound by the following hypothesis, it is thought that administration of the CCS of the present invention to a mammal stimulates an immune response against one or more secreted antigens, such as EspA and Tir, that blocks attachment of the EHEC to intestinal epithelial cells.

Accordingly, it is an object of the present invention to provide a vaccine effective to stimulate an immune response against EHEC secreted antigens, thereby treating and/or preventing EHEC disease in a mammal.

Another object is to provide a vaccine effective to reduce, prevent and/or eliminate EHEC colonization of a ruminant or other mammal.

Another object is to reduce the number of animals shedding EHEC into the environment.

Another object is to reduce the number of EHEC shed into the environment by an infected animal.

Another object is reduce the time during which EHEC are shed into the environment by an infected animal.

Another object is reduce EHEC contamination of the environment.

Another object is reduce EHEC contamination of meat and/or water.

Another object is to treat, prevent and/or reduce EHEC infections in humans.

Another object is to provide a vaccine effective as an adjunct to other biological anti-EHEC agents.

Another object is to provide a vaccine effective as an adjunct to chemical anti-EHEC agents.

Another object is to provide a vaccine effective as an adjunct to biologically engineered anti-EHEC agents.

Another object is to provide a vaccine effective as an adjunct to nucleic acid-based anti-EHEC agents.

Another object is to provide a vaccine effective as an adjunct to recombinant protein anti-EHEC agents.

Another object is to provide a vaccination schedule effective to reduce EHEC colonization of a ruminant.

Another object is to provide a vaccination schedule effective to reduce EHEC shedding by a ruminant.

Another object is to provide a vaccine effective to reduce EHEC O157 colonization of cattle, such as colonization of EHEC O157:H7 and/or EHEC O157:NM.

Another object is to provide a vaccine effective to prevent EHEC O157 colonization of cattle, such as colonization of EHEC O157:H7 and/or EHEC O157:NM.

Another object is to provide a vaccine effective to eliminate EHEC O157 colonization of cattle, such as colonization of EHEC O157:H7 and/or EHEC O157:NM.

Another object is to reduce the number of cattle shedding EHEC O157 into the environment, such as shedding of EHEC O157:H7 and/or EHEC O157:NM.

Another object is to reduce the number of EHEC O157 shed into the environment by infected cattle, such as shedding of EHEC O157:H7 and/or EHEC O157:NM.

Another object is reduce the time during which EHEC O157 are shed into the environment by infected cattle, such as shedding of EHEC O157:H7 and/or EHEC O157:NM.

Another object is to provide a vaccine effective as an adjunct to other anti-EHEC O157 agents.

Another object is to provide a vaccination schedule effective to reduce EHEC O157 colonization of cattle.

Another object is to provide a vaccination schedule effective to reduce EHEC O157 shedding by cattle.

Thus, in one embodiment, the invention is directed to a vaccine composition comprising an enterohemorragic *Escherichia coli* (EHEC) cell culture supernatant and an immunological adjuvant. In certain embodiments, the EHEC is EHEC O157:H7 and/or EHEC O157:NM. In additional embodiments, the immunological adjuvant comprises an oil-in-water emulsion, such as a mineral oil and dimethyldioctadecylammonium bromide. In yet additional embodiments, the immunological adjuvant is VSA3. The VSA3 may be present at a concentration of about 20% to about 40% (v/v), such as at a concentration of 30% (v/v).

In still further embodiments, the vaccine composition further comprises one or more recombinant or purified EHEC secreted antigens selected from the group consisting of EspA, EspB, EspD and Tir. In other embodiments, EspA+Tir comprise at least 20% of the cell protein present in the composition.

In further embodiments, the subject invention is directed to methods for eliciting an immunological response in a mammal against a secreted enterohemorragic *Escherichia coli* (EHEC) antigen. The method comprises administering to the mammal a therapeutically effective amount of a composition comprising an EHEC cell culture supernatant. In certain embodiments, the EHEC is EHEC O157:H7 and/or EHEC O157:NM. In additional embodiments, the mammal is a human or a ruminant, such as a bovine subject. In yet further embodiments, the composition further comprises an immunological adjuvant, such as an oil-in-water emulsion which comprises e.g., a mineral oil and dimethyldioctadecylammonium bromide. In additional embodiments, the adjuvant is VSA3. The compositions may further comprise one or more recombinant or purified EHEC secreted antigens selected from the group consisting of EspA, EspB, EspD and Tir. In other embodiments, EspA+Tir comprise at least 20% of the cell protein present in the composition.

In another embodiment, the invention is directed to a method for eliciting an immunological response in a ruminant against a secreted enterohemorragic *Escherichia coli* O157:H7 (EHEC O157:H7) antigen. The method comprises administering to the ruminant a therapeutically effective amount of a composition comprising an EHEC O157:H7 cell culture supernatant and VSA3. In additional embodiments, VSA3 is present in the composition at a concentration of about 20% to about 40% (v/v), such as at about 30% (v/v).

In still a further embodiment, the invention is directed to a method for reducing colonization of enterohemorragic *Escherichia coli* (EHEC) in a ruminant comprising administering to the ruminant a therapeutically effective amount of a composition comprising an EHEC cell culture supernatant and an immunological adjuvant.

In yet another embodiment, the invention is directed to a method for reducing shedding of enterohemorragic *Escherichia coli* (EHEC) from a ruminant comprising administering to the ruminant a therapeutically effective amount of a composition comprising an EHEC cell culture supernatant and an immunological adjuvant.

These and other aspects of the present invention will become evident upon reference to the following detailed description and attached drawings. In addition, various references are set forth herein which describe in more detail certain procedures or compositions, and are therefore incorporated by reference in their entireties.

BRIEF DESCRIPTION OF THE DRAWINGS

FIG. 1 shows the electrophoretic profile of CCS proteins separated by polyacrylamide gel electrophoresis.

FIG. 2 shows the electrophoretic profile of recombinant EspA, Tir, EspB and Intimin separated by polyacrylamide gel electrophoresis.

FIG. 3 shows fecal shedding of EHEC O157:H7 by cattle immunized with a CCS vaccine following EHEC O157:H7 challenge.

FIG. 4 depicts reactivation of fecal shedding of EHEC O157:H7 in previously infected cattle.

FIG. 5 shows the serological response to immunization with recombinant EspA+Tir vaccine and with recombinant EspB+Intimin vaccine.

FIG. 6 depicts fecal shedding of EHEC O157:H7 following immunization with recombinant EspA+Tir vaccine and with saline vaccine.

FIG. 7 shows the number of animals shedding *E. coli* O157:H7 on each day of the vaccine trial described in Example 6. Bacteria were detected by direct plating of fecal samples which had been resuspended in saline on Sorbitol MaConkey agar supplemented with cefixime and tellurite. Solid bars, placebo group; hatched bars, EHEC vaccine group.

FIG. 8 shows an immunoblot analysis of sera from vaccinated animals against EHEC secreted proteins. Each blot contains secreted proteins from wild-type *E. coli* O157:H7 (EHEC), type III secretion mutant (ΔSepB), tir mutant (ΔTir) and a purified glutathione-s-transferase:Tir fusion protein (GST-Tir). Proteins were separated by SDS-10%

PAGE and stained with Coomassie blue (A, upper left panel) or transferred to nitrocellulose and probed with representative sera from animals which received 3 immunizations with each vaccine formulation (A, upper panels). The lower four panels (B) were probed with sera from one representative animal which received the EHEC vaccine, taken on days 0, 21, 25 and 49 of the trial.

Figure 9:
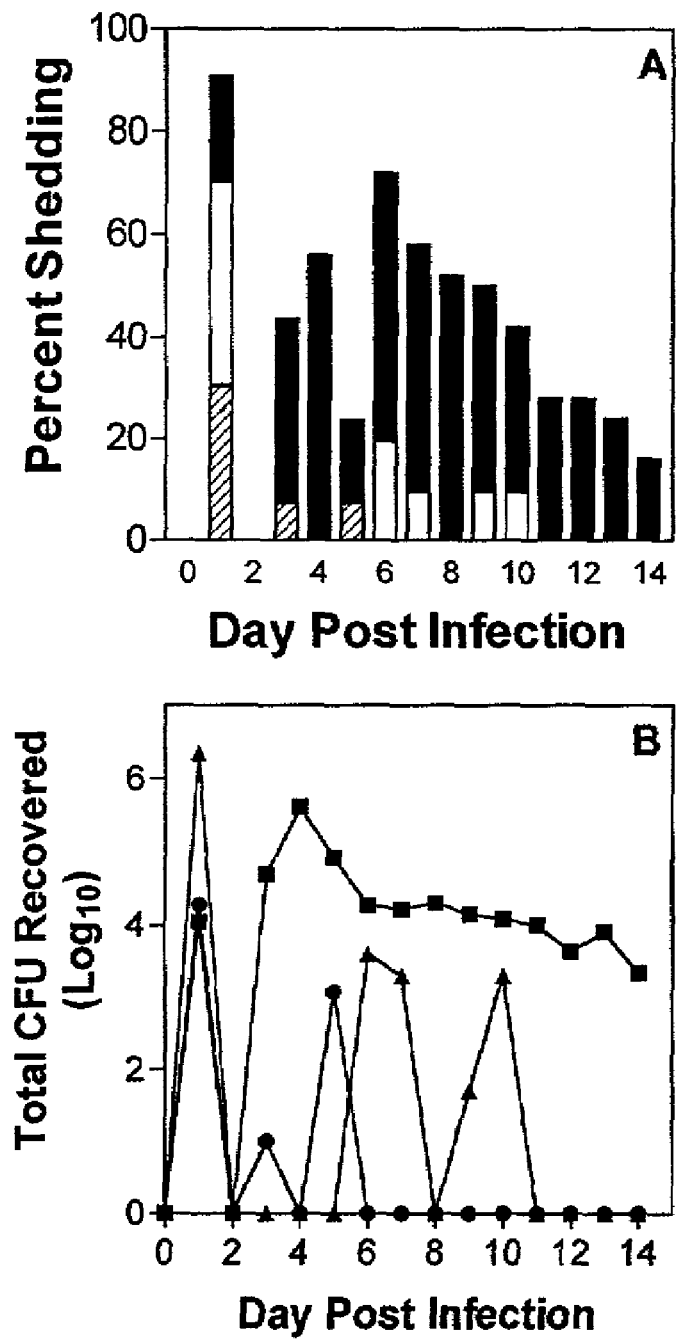

FIG. 9 shows the percentage of each group of animals shedding *E. coli* O157:H7(Panel A) and the total number of bacteria recovered (Panel B) on each day of the trial described in Example 6. Bacteria were detected in feces by plating on Sorbitol MaConkey agar supplemented with cefixime and tellurite following immunomagnetic enrichment as described in J. Van Donkersgoed et al., *Can. Vet. J.* (2001) 42:714. (A) Solid bars, placebo; hatched bars, EHEC vaccine; open bars, ΔTir vaccine. (B) ■, placebo group; ●, EHEC vaccine; ▲, ΔTir vaccine.

DETAILED DESCRIPTION OF THE INVENTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual,* Vols. I, II and III, Second Edition (1989); Perbal, B., *A Practical Guide to Molecular Cloning* (1984); the series, *Methods In Enzymology* (S. Colowick and N. Kaplan eds., Academic Press, Inc.); and *Handbook of Experimental Immunology,* Vols. I–IV (D. M. Weir and C. C. Blackwell eds., 1986, Blackwell Scientific Publications).

All publications, patents and patent applications cited herein, whether supra or infra, are hereby incorporated by reference in their entirety.

A. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an EHEC bacterium" includes a mixture of two or more such bacteria, and the like.

As used herein, the term EHEC "cell culture supernatant" or "CCS" refers to a supernatant derived from a cell culture of one or more EHEC serotypes, which supernatant is substantially free of EHEC bacterial cells or the lysate of such cells, and which contains a mixture of EHEC antigens that have been secreted into the growth media. Generally, an EHEC "CCS" will contain at least the secreted antigens EspA, EspB, EspD and Tir, and fragments or aggregates thereof. The CCS of the present invention may also include other secreted proteins, such as EspF and MAP, one or both of Shiga toxins 1 and 2, as well as EspP which is an approximately 100 kDa protein which is not secreted by the type III system. The proteins can be present in a native form, or a denatured or degraded form, so long as the CCS still functions to stimulate an immune response in the host subject such that EHEC disease is lessened or prevented, and/or colonization of EHEC is lessened or suppressed. In some instances, a CCS may be supplemented with additional recombinant or purified secreted antigens, such as with additional EspA, EspB, EspD and/or Tir, as well as with any of the other secreted proteins, and may also be supplemented with Intimin. In certain embodiments, EspA+Tir will comprise at least 20% of the cell culture supernatant protein.

As used herein, a "recombinant" EHEC secreted protein, such as rEspA, rEspB, rEspD and rTir, as well as the "recombinant Intimin", refers to the full-length polypeptide sequence, fragments of the reference sequence or substitutions, deletions and/or additions to the reference sequence, so long as the proteins retain at least one specific epitope or activity. Generally, analogs of the reference sequence will display at least about 50% sequence identity, preferably at least about 75% to 85% sequence identity, and even more preferably about 90% to 95% or more sequence identity, to the full-length reference sequence. See, e.g., GenBank Accession Nos. AE005594, AE005595, AP002566, AE005174, NC_002695, NC_002655 for the complete sequence of the *E. coli* O157:H7 genome, which includes the sequences of the various O157:H7 secreted proteins. See, e.g., International Publication No. WO 97/40063, as well as GenBank Accession Nos. Y13068, U80908, U5681, Z54352, AJ225021, AJ225020, AJ225019, AJ225018, AJ225017, AJ225016, AJ225015, AF022236 and AF200363 for the nucleotide and amino acid sequences of EspA from a number of *E. coli* serotypes. See, e.g., International Publication No. WO 99/24576, as well as GenBank Accession Nos. AF125993, AF132728, AF045568, AF022236, AF70067, AF070068, AF013122, AF200363, AF113597, AF070069, AB036053, AB026719, U5904 and U59502, for the nucleotide and amino acid sequences of Tir from a number of *E. coli* serotypes. See, e.g., GenBank Accession Nos. U32312, U38618, U59503, U66102, AF081183, AF081182, AF130315, AF339751, AJ308551, AF301015, AF329681, AF319597, AJ275089–AJ275113 for the nucleotide and amino acid sequences of Intimin from a number of *E. coli* serotypes. See, e.g., GenBank Accession Nos. U80796, U65681, Y13068, Y13859, X96953, X99670, X96953, Z21555, AF254454, AF254455, AF254456, AF254457, AF054421, AF059713, AF144008, AF144009 for the nucleotide and amino acid sequences of EspB from a number of *E. coli* serotypes. See, e.g., GenBank Accession Nos. Y13068, Y13859, Y17875, Y17874, Y09228, U65681, AF054421 and AF064683, for the nucleotide and amino acid sequences of EspD from a number of *E. coli* serotypes.

"Homology" refers to the percent similarity between two polynucleotide or two polypeptide moieties. Two DNA, or two polypeptide sequences are "substantially homologous" to each other when the sequences exhibit at least about 80%–85%, preferably at least about 90%, and most preferably at least about 95%–98% sequence similarity over a defined length of the molecules. As used herein, substantially homologous also refers to sequences showing complete identity to the specified DNA or polypeptide sequence.

Percent sequence identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, DC, which adapts the local homology algorithm of Smith and Waterman (1981) *Advances in Appl. Math.* 2:482–489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

As used herein, "vaccine" refers to a CCS composition that serves to stimulate an immune response to an EHEC antigen, such as a type III secreted EHEC antigen, therein. The immune response need not provide complete protection and/or treatment against EHEC infection or against colonization and shedding of EHEC. Even partial protection against colonization and shedding of EHEC bacteria will find use herein as shedding and contaminated meat production will still be reduced. In some cases, a vaccine will include an immunological adjuvant in order to enhance the immune response. The term "adjuvant" refers to an agent which acts in a nonspecific manner to increase an immune response to a particular antigen or combination of antigens, thus reducing the quantity of antigen necessary in any given vaccine, and/or the frequency of injection necessary in order to generate an adequate immune response to the antigen of interest. See, e.g., A. C. Allison *J. Reticuloendothel. Soc.* (1979) 26:619–630. Such adjuvants are described further below.

As used herein, "colonization" refers to the presence of EHEC in the intestinal tract of a mammal, such as a ruminant.

As used herein, "shedding" refers to the presence of EHEC in feces.

As used herein, "therapeutic amount", "effective amount" and "amount effective to" refer to an amount of vaccine effective to elicit an immune response against a secreted antigen present in the CCS, thereby reducing or preventing EHEC disease, and/or EHEC colonization of a mammal such as a ruminant; and/or reducing the number of animals shedding EHEC; and/or reducing the number of EHEC shed by an animal; and/or, reducing the time period of EHEC shedding by an animal.

As used herein, "immunization" or "immunize" refers to administration of CCS, with or without additional recombinant or purified EHEC antigens such as EspA, Tir, EspB, EspD, and/or Intimin, in an amount effective to stimulate the immune system of the animal to which the CCS is administered, to elicit an immunological response against one or more of the secreted antigens present in the CCS.

The term "epitope" refers to the site on an antigen or hapten to which specific B cells and/or T cells respond. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that EHEC disease is lessened and/or prevented; resistance of the intestine to colonization with EHEC is imparted; the number of animals shedding EHEC is reduced; the number of EHEC shed by an animal is reduced; and/or the time period of EHEC shedding by an animal is reduced.

The terms "immunogenic" protein or polypeptide refer to an amino acid sequence which elicits an immunological response as described above. An "immunogenic" protein or polypeptide, as used herein, includes the full-length sequence of the particular EHEC protein in question, analogs thereof, aggregates, or immunogenic fragments thereof. By "immunogenic fragment" is meant a fragment of a secreted EHEC protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols,* supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

Immunogenic fragments, for purposes of the present invention, will usually include at least about 3 amino acids, preferably at least about 5 amino acids, more preferably at least about 10–15 amino acids, and most preferably 25 or more amino acids, of the parent EHEC secreted protein molecule. There is no critical upper limit to the length of the fragment, which may comprise nearly the full-length of the protein sequence, or even a fusion protein comprising two or more epitopes of the particular EHEC secreted protein.

"Native" proteins or polypeptides refer to proteins or polypeptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

The term "treatment" as used herein refers to either (i) the prevention of infection or reinfection (prophylaxis), or (ii) the reduction or elimination of symptoms of the disease of interest (therapy).

By "mammalian subject" is meant any member of the class Mammalia, including humans and all other mammary gland possessing animals (both male and female), such as ruminants, including, but not limited to, bovine, porcine and *Ovis* (sheep and goats) species. The term does not denote a particular age. Thus, adults, newborns, and fetuses are intended to be covered.

B. General Methods

Central to the present invention is the discovery that cell culture supernatants derived from EHEC cultures which contain EHEC secreted antigens, produce an immune response in animals to which they are administered and thereby provide protection against EHEC infection, such as protection against colonization. In certain embodiments, the compositions comprise a mixture of EHEC secreted antigens, including but not limited to EspA, EspB, EspD and/or Tir. The CCS of the present invention may also include other secreted proteins, such as EspF and MAP, one or both of Shiga toxins 1 and 2, as well as EspP which is an approximately 100 kDa protein which is not secreted by the type III system. In other embodiments, the CCS is supplemented with additional recombinant or purified EHEC antigens, such as with additional EspA, EspB, EspD, Tir, Intimin, and the like. In certain embodiments, EspA+Tir comprise at least 20% of the cell culture supernatant protein. The compositions can comprise cell culture supernatants and additional adjuvants from more than one EHEC serotype to provide protection against multiple EHEC organisms. Moreover, a pharmaceutically acceptable adjuvant may be administered with the cell culture supernatant. The compositions are administered in an amount effective to elicit an immune response to one or more of the secreted antigens, thereby reducing or eliminating EHEC infection. In some instances, EHEC colonization of the animal is reduced or eliminated. In preferred embodiments, the animal is a cow or a sheep or other ruminant. In particularly preferred embodiments, the cell culture supernatant is derived from a cell culture of EHEC O157:H7 or EHEC O157:NM.

Immunization with CCS stimulates the immune system of the immunized animal to produce antibodies against one or more secreted EHEC antigens, such as EspA, EspB, EspD and Tir, that block EHEC attachment to intestinal epithelial cells, interfere with EHEC colonization and, thereby, reduce EHEC shedding by the animal. This reduction in EHEC shedding results in a reduction in EHEC contamination of food and water and a reduction in EHEC-caused disease in humans. Moreover, the unexpected and surprising ability of CCS immunization to prevent, reduce and eliminate EHEC colonization and shedding by cattle addresses a long-felt unfulfilled need in the medical arts, and provides an important benefit for humans.

Additionally, the CCS of the present invention can be used to treat or prevent EHEC infections in other mammals such as humans. If used in humans, the CCS can be produced from a mutated EHEC which has been engineered to knock out one or both of the Shiga toxins 1 and 2 in order to reduce toxicity.

As explained above, the therapeutic effectiveness of CCS can be increased by adding thereto one or more of the secreted antigens in recombinant or purified form, such as by adding recombinant or purified EspA, EspB, EspD, Tir, and the like, fragments thereof and/or analogs thereof. Intimin may also be added. Other methods to increase the therapeutic effectiveness of CCS include, but are not limited to, complexing the CCS to natural or synthetic carriers and administering the CCS, before, at the same time as, or after another anti-EHEC agent. Such agents include, but are not limited to, biological, biologically engineered, chemical, nucleic acid based and recombinant protein anti-EHEC agents.

CCS from pathogenic bacteria, other than serotypes of EHEC, that require proteins such as EspA and Tir to colonize a host, can also be used to stimulate the immune system of an animal to produce antibodies against secreted EHEC antigens that reduce bacterial binding to intestinal epithelial cells of the animal. These bacterial species include, but are not limited to *Citrotobacter rodentium*.

The CCS for use herein may be obtained from cultures of any EHEC serotype, including, without limitation, EHEC serotypes from serogroups O157, O158, O5, O8, O18, O26, O45, O48, O52, O55, O75, O76, O78, O84,O91, O103, O104, O111, O113, O114, O116, O118, O119, O121, O125, O28, O145, O146, O163, O165. Such EHEC serotypes are readily obtained from sera of infected animals. Methods for isolated EHEC are well known in the art. See, e.g., Elder et al., *Proc. Natl. Acad. Sci. USA* (2000) 97:2999; Van Donkersgoed et al., *Can. Vet. J.* (1999) 40:332; Van Donkersgoed et al., *Can. Vet. J.* (2001) 42:714. Generally, such methods entail direct plating on sorbitol MacConkey agar supplemented with cefixime and tellurite or immunomagnetic enrichment followed by plating on the same media. Moreover, CCS may be obtained from EHEC serotypes that have been genetically engineered to knock-out expression of Shiga toxins 1 and/or 2, in order to reduce toxicity.

Generally, CCS is produced by culturing EHEC bacteria in a suitable medium, under conditions that favor type III antigen secretion. Suitable media and conditions for culturing EHEC bacteria are known in the art and described in e.g., U.S. Pat. Nos. 6,136,554 and 6,165,743 (incorporated herein by reference in their entireties), as well as in Li et al., *Infec. Immun.* (2000) 68:5090–5095; Fey et al., *Emerg. Infect. Dis.* (2000) Volume 6. A particularly preferable method of obtaining CCS is by first growing organisms in Luria-Bertani (LB) medium for a period of about 8 to 48 hours, preferably about 12 to 24 hours, and diluting this culture about 1:5 to 1:50, preferably 1:5 to 1:25, more preferably about 1:10, into M-9 minimal medium supplemented with 20–100 mM $NaHCO_3$, preferably 30–50 mM, most preferably about 44 mM $NaHCO_3$, 4–20 mM $MgSO_4$, preferably 5–10 mM and most preferably about 8 mM $MgSO_4$, 0.1 to 1.5% glucose, preferable 0.2 to 1%, most preferably 0.4% glucose and 0.05 to 0.5% Casamino Acids, preferably 0.07 to 0.2%, most preferably about 0.1% Casamino Acids. Cultures are generally maintained at about 37 degrees C. in 2–10% $CO_2$, preferably about 5% $CO_2$, to an optical density of about 600 nm of 0.7 to 0.8. Whole cells are then removed by centrifugation and the supernatant can be concentrated, e.g., 10–1000 fold or more, such as 100-fold, using dialysis, ultrafiltration and the like. Total protein is easily determined using methods well known in the art.

As explained above, the CCS can be supplemented with additional EHEC secreted proteins, such as EspA, EspB, EspD and/or Tir. Intimin may also be added. These proteins can be produced recombinantly using techniques well known in the art. See, e.g., International Publication Nos. WO 97/40063 and WO 99/24576 for a description of the production of representative recombinant EHEC secreted proteins. In particular, the sequences for EspA, EspB, EspD, Tir and Intimin from various serotypes are known and described. See, e.g., GenBank Accession Nos. AE005594, AE005595, AP002566, AE005174, NC_002695, NC_002655 for the complete sequence of the *E. coli* O157:H7 genome, which includes the sequences of the various O157:H7 secreted proteins. See, e.g., International Publication No. WO 97/40063, as well as GenBank Accession Nos. Y13068, U80908, U5681, Z54352, AJ225021, AJ225020, AJ225019, AJ225018, AJ225017, AJ225016, AJ225015, AF022236 and AF200363 for the nucleotide and amino acid sequences of EspA from a number of *E. coli* serotypes. See, e.g., International Publication No. WO 99/24576, as well as GenBank Accession Nos. AF125993, AF132728, AF045568, AF022236, AF70067, AF070068, AF013122, AF200363, AF113597, AF070069, AB036053, AB026719, U5904 and U59502, for the nucleotide and amino acid sequences of Tir from a number of *E. coli* serotypes. See, e.g., GenBank Accession Nos. U32312, U38618, U59503, U66102, AF081183, AF081182, AF130315, AF339751, AJ308551, AF301015, AF329681, AF319597, AJ275089–AJ275113 for the nucleotide and amino acid sequences of Intimin from a number of *E. coli* serotypes. See, e.g., GenBank Accession Nos. U80796, U65681, Y13068, Y13859, X96953, X99670, X96953, Z21555, AF254454, AF254455, AF254456, AF254457, AF054421, AF059713, AF144008, AF144009 for the nucleotide and amino acid sequences of EspB from a number of *E. coli* serotypes. See, e.g., GenBank Accession Nos. Y13068, Y13859, Y17875, Y17874, Y09228, U65681, AF054421 and AF064683, for the nucleotide and amino acid sequences of EspD from a number of *E. coli* serotypes.

These sequences can be used to design oligonucleotide probes and used to screen genomic or cDNA libraries for genes from other *E. coli* serotypes. The basic strategies for preparing oligonucleotide probes and DNA libraries, as well as their screening by nucleic acid hybridization, are well known to those of ordinary skill in the art. See, e.g., *DNA Cloning:* Vol. I, supra; *Nucleic Acid Hybridization,* supra; *Oligonucleotide Synthesis,* supra; Sambrook et al., supra. Once a clone from the screened library has been identified by positive hybridization, it can be confirmed by restriction enzyme analysis and DNA sequencing that the particular library insert contains a type III gene or a homolog thereof. The genes can then be further isolated using standard techniques and, if desired, PCR approaches or restriction enzymes employed to delete portions of the full-length sequence.

Similarly, genes can be isolated directly from bacteria using known techniques, such as phenol extraction and the sequence further manipulated to produce any desired alterations. See, e.g., Sambrook et al., supra, for a description of techniques used to obtain and isolate DNA. Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; *DNA Cloning,* supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning,* supra; *Nucleic Acid Hybridization,* supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis,* and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda,* and *Trichoplusia ni.*

Depending on the expression system and host selected, the proteins of the present invention are produced by culturing host cells transformed by an expression vector described above under conditions whereby the protein of interest is expressed. The protein is then isolated from the host cells and purified. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, New York, (1980), pp. 3–254, for solid phase peptide synthesis techniques; and M. Bodansky, *Principles of Peptide Synthesis,* Springer-Verlag, Berlin (1984) and E. Gross and J. Meienhofer, Eds., *The Peptides: Analysis, Synthesis, Biology,* supra, Vol. 1, for classical solution synthesis. Chemical synthesis of peptides may be preferable if a small fragment of the antigen in question is capable of raising an immunological response in the subject of interest.

Once the above cell culture supernatants and, if desired, additional recombinant and/or purified proteins are produced, they are formulated into compositions for delivery to a mammalian subject. The CCS is administered alone, or mixed with a pharmaceutically acceptable vehicle or excipient. Suitable vehicles are, for example, water, saline, dextrose, glycerol, ethanol, or the like, and combinations thereof. In addition, the vehicle may contain minor amounts of auxiliary substances such as wetting or emulsifying agents, pH buffering agents, or adjuvants in the case of vaccine compositions, which enhance the effectiveness of the vaccine. Suitable adjuvants are described further below. The compositions of the present invention can also include ancillary substances, such as pharmacological agents, cytokines, or other biological response modifiers.

As explained above, vaccine compositions of the present invention may include adjuvants to further increase the immunogenicity of one or more of the EHEC antigens. Such adjuvants include any compound or compounds that act to increase an immune response to an EHEC antigen or combination of antigens, thus reducing the quantity of antigen necessary in the vaccine, and/or the frequency of injection necessary in order to generate an adequate immune response. Adjuvants may include for example, emulsifiers, muramyl dipeptides, avridine, aqueous adjuvants such as aluminum hydroxide, chitosan-based adjuvants, and any of the various saponins, oils, and other substances known in the art, such as AMPHIGEN™ (AMPHIGEN™ comprises deoiled lecithin dissolved in an oil, usually light liquid paraffin. In vaccine preparations AMPHIGEN™ is dispersed in an aqueous solution or suspension of the immunizing antigen as an oil-in-water emulsion), LPS, bacterial cell wall extracts, bacterial DNA, synthetic oligonucleotides and combinations thereof (Schijns et al., Curr. Opi. Immunol. (2000) 12:456), Mycobacterial phlei (M. phlei} cell wall extract (MCWE) (U.S. Pat. No. 4,744,984), M. phlei DNA (M-DNA), M-DNA-M phlei cell wall complex (MCC). For example, compounds which may serve as emulsifiers herein include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate. Synthetic cationic agents include, for example, cetyltrimethylammonium bromide, while synthetic nonionic agents are exemplified by glyceryl esters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil may be a mineral oil, a vegetable oil, or an animal oil. Mineral oil, or oil-in-water emulsions in which the oil component is mineral oil are preferred. In this regard, a "mineral oil" is defined herein as a mixture of liquid hydrocarbons obtained from petrolatum via a distillation technique; the term is synonymous with "liquid paraffin," "liquid petrolatum" and "white mineral oil." The term is also intended to include "light mineral oil," i.e., an oil which is similarly obtained by distillation of petrolatum, but which has a slightly lower specific gravity than white mineral oil. See, e.g., *Remington's Pharmaceutical Sciences,* supra. A particularly preferred oil component is the oil-in-water emulsion sold under the trade name of EMULSIGEN PLUS™ (comprising a light mineral oil as well as 0.05% formalin, and 30 mcg/mL gentamicin as preservatives), available from MVP Laboratories, Ralston, Nebr. Suitable animal oils include, for example, cod liver oil, halibut oil, menhaden oil, orange roughy oil and shark liver oil, all of which are available commercially. Suitable vegetable oils, include, without limitation, canola oil, almond oil, cottonseed oil, corn oil, olive oil, peanut oil, safflower oil, sesame oil, soybean oil, and the like.

Alternatively, a number of aliphatic nitrogenous bases can be used as adjuvants with the vaccine formulations. For example, known immunologic adjuvants include amines, quaternary ammonium compounds, guanidines, benzamidines and thiouroniums (Gall, D. (1966) *Immunology* 11:369–386). Specific compounds include dimethyldioctadecylammonium bromide (DDA) (available from Kodak) and N,N-dioctadecyl-N,N-bis(2-hydroxyethyl)propanediamine ("avridine"). The use of DDA as an immunologic adjuvant has been described; see, e.g., the Kodak Laboratory Chemicals Bulletin 56(1):1–5 (1986); *Adv. Drug Deliv. Rev.* 5(3):163–187 (1990); *j. controlled Release* 7:123–132 (1988); *Clin. Exp. Immunol.* 78(2):256–262 (1989); *J. Immunol. Methods* 97(2):159–164 (1987); *Immunology* 58(2):245–250 (1986); and *Int. Arch. Allergy Appl. Immunol.* 68(3):201–208 (1982). Avridine is also a well-known adjuvant. See, e.g., U.S. Pat. No. 4,310,550 to Wolff, III et al., which describes the use of N,N-higher alkyl-N',N'-bis (2-hydroxyethyl)propane diamines in general, and avridine in particular, as vaccine adjuvants. U.S. Pat. No. 5,151,267 to Babiuk, and Babiuk et al. (1986) *Virology* 159:57–66, also relate to the use of avridine as a vaccine adjuvant.

Particularly preferred for use herein is an adjuvant known as "VSA3" which is a modified form of the EMULSIGEN PLUS™ adjuvant which includes DDA (see, U.S. Pat. No. 5,951,988, incorporated herein by reference in its entirety).

CCS vaccine compositions can be prepared by uniformly and intimately bringing into association the CCS preparations and the adjuvant using techniques well known to those skilled in the art including, but not limited to, mixing, sonication and microfluidation. The adjuvant will preferably comprise about 10 to 50% (v/v) of the vaccine, more preferably about 20 to 40% (v/v) and most preferably about 20 to 30% or 35% (v/v), or any integer within these ranges.

The compositions of the present invention are normally prepared as injectables, either as liquid solutions or suspensions, or as solid forms which are suitable for solution or suspension in liquid vehicles prior to injection. The preparation may also be prepared in solid form, emulsified or the active ingredient encapsulated in liposome vehicles or other particulate carriers used for sustained delivery. For example, the vaccine may be in the form of an oil emulsion, water in oil emulsion, water-in-oil-in-water emulsion, site-specific emulsion, long-residence emulsion, sticky-emulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the vaccine.

Furthermore, the polypeptides may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Actual methods of preparing such dosage forms are known, or will be apparent, to those skilled in the art. See, e.g., *Remington's Pharmaceutical Sciences,* Mack Publishing Company, Easton, Pa., 18th edition, 1990.

The composition is formulated to contain an effective amount of secreted EHEC antigen, the exact amount being readily determined by one skilled in the art, wherein the amount depends on the animal to be treated and the capacity of the animal's immune system to synthesize antibodies. The composition or formulation to be administered will contain a quantity of one or more secreted EHEC antigens adequate to achieve the desired state in the subject being treated. For purposes of the present invention, a therapeutically effective amount of a vaccine comprising CCS with or without added recombinant and/or purified secreted EHEC antigens, contains about 0.05 to 1500 μg secreted EHEC protein, preferably about 10 to 1000 μg secreted EHEC protein, more preferably about 30 to 500 μg and most preferably about 40 to 300 μg, or any integer between these values. EspA+Tir, as well as other EHEC antigens, may comprise about 10% to 50% of total CCS protein, such as about 15% to 40% and most preferably about 15% to 25%. If supplemented with rEspA+rTir, the vaccine may contain about 5 to 500 μg of protein, more preferably about 10 to 250 μg and most preferably about 20 to 125 μg.

Routes of administration include, but are not limited to, oral, topical, subcutaneous, intramuscular, intravenous, subcutaneous, intradermal, transdermal and subdermal. Depending on the route of administration, the volume per dose is preferably about 0.001 to 10 ml, more preferably about 0.01 to 5 ml, and most preferably about 0.1 to 3 ml. Vaccine can be administered in a single dose treatment or in multiple dose treatments (boosts) on a schedule and over a time period appropriate to the age, weight and condition of the subject, the particular vaccine formulation used, and the route of administration.

Any suitable pharmaceutical delivery means may be employed to deliver the compositions to the vertebrate subject. For example, conventional needle syringes, spring or compressed gas (air) injectors (U.S. Pat. No. 1,605,763 to Smoot; U.S. Pat. No. 3,788,315 to Laurens; U.S. Pat. No. 3,853,125 to Clark et al.; U.S. Pat. No. 4,596,556 to Morrow et al.; and U.S. Pat. No. 5,062,830 to Dunlap), liquid jet injectors (U.S. Pat. No. 2,754,818 to Scherer; U.S. Pat. No. 3,330,276 to Gordon; and U.S. Pat. No. 4,518,385 to Lindmayer et al.), and particle injectors (U.S. Pat. No. 5,149,655 to McCabe et al. and U.S. Pat. No. 5,204,253 to Sanford et al.) are all appropriate for delivery of the compositions.

If a jet injector is used, a single jet of the liquid vaccine composition is ejected under high pressure and velocity, e.g., 1200–1400 PSI, thereby creating an opening in the skin and penetrating to depths suitable for immunization.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

C. Experimental

EXAMPLE 1

Preparation of Cell Culture Supernatant (CCS)

Wild type EHEC O157:H7 were grown under conditions to maximize the synthesis of CCS proteins (Li et al., *Infect. Immun.* (2000) 68:5090). Briefly, an overnight standing culture of EHEC O157:H7 was grown in Luria-Bertani (LB) medium overnight at 37° C. (±5% $CO_2$). The culture was diluted 1:10 in M-9 minimal medium supplemented with 0.1% Casamino Acids, 0.4% glucose, 8 mM $MgSO_4$ and 44 mM $NaHCO_3$. Cultures were grown standing at 37° C. in 5% $CO_2$ to an optical density at 600 nm of 0.7 to 0.8 (6–8 h). Bacteria were removed by centrifugation at 8000 rpm for 20 min at 4° C. The supernatant was concentrated 100 fold by ultrafiltration and total protein was determined by the bicinchoninic acid protein assay method.

FIG. 1 shows molecular weight markers (lane 1) and a typical CCS protein profile obtained by electrophoresis of CCS in a SDS-10% polyacrylamide gel (SDS-PAGE) followed by Coomassie blue staining (lane 2). The positions of EspA (25 kD), EspB/EspD (40 kD), undegraded Tir (70 kD) and degraded Tir (55 kD) are indicated. As determined by densitometric analysis using an HP Scanjet 5100C and the ID software program from Advance American Biotechnology (Fullerton, Calif., USA), EspA was about 5% undegraded Tir about 20% and degraded Tir about 6% of the total protein. However, the percentages of proteins determined by densitometric analysis of Coomassie blue stained SDS-polyacrylamide gels is not exact due to variations in background staining, variations in the uptake of the Coomassie blue stain, variations in the density of the bands, and other factors known to those skilled in the art.

EXAMPLE 2

Preparation of Recombinant Proteins

The genes coding for EspA, EspB, Intimin and Tir were isolated (Li et al., *Infect. Immun.* (2000) 68:5090). A clinical isolate of EHEC O157:H7 was used as the source of DNA. EspA, EspB, Tir, and the region of eae encoding the 280 carboxyl-terminal amino acids of Intimin were amplified from chromosomal DNA using PCR to introduce unique restriction sites, followed by cloning into appropriate plasmids. The resulting plasmids were cleaved and ligated to create histidine-tagged fusions. Plasmids were electrocuted into an expression strain of *E. coli* and the *E. coli* were propagated (Ngeleka et al., *Infect. Immun.* (1996) 64:3118). Gene expression was driven using the Tac promoter following IPTG (isopropyl-β-D-thiogalactopyranoside) induction. Bacteria were pelleted, resuspended in Tris-buffered saline and lysed by sonication. The lysate was centrifuged to remove insoluble material and the histidine-tagged proteins were purified by passage through a solid-phase nickel affinity chromatography column that specifically binds proteins containing the histidine tag. All recombinant protein preparations were stored at −20° C. until use.

Figure 2:
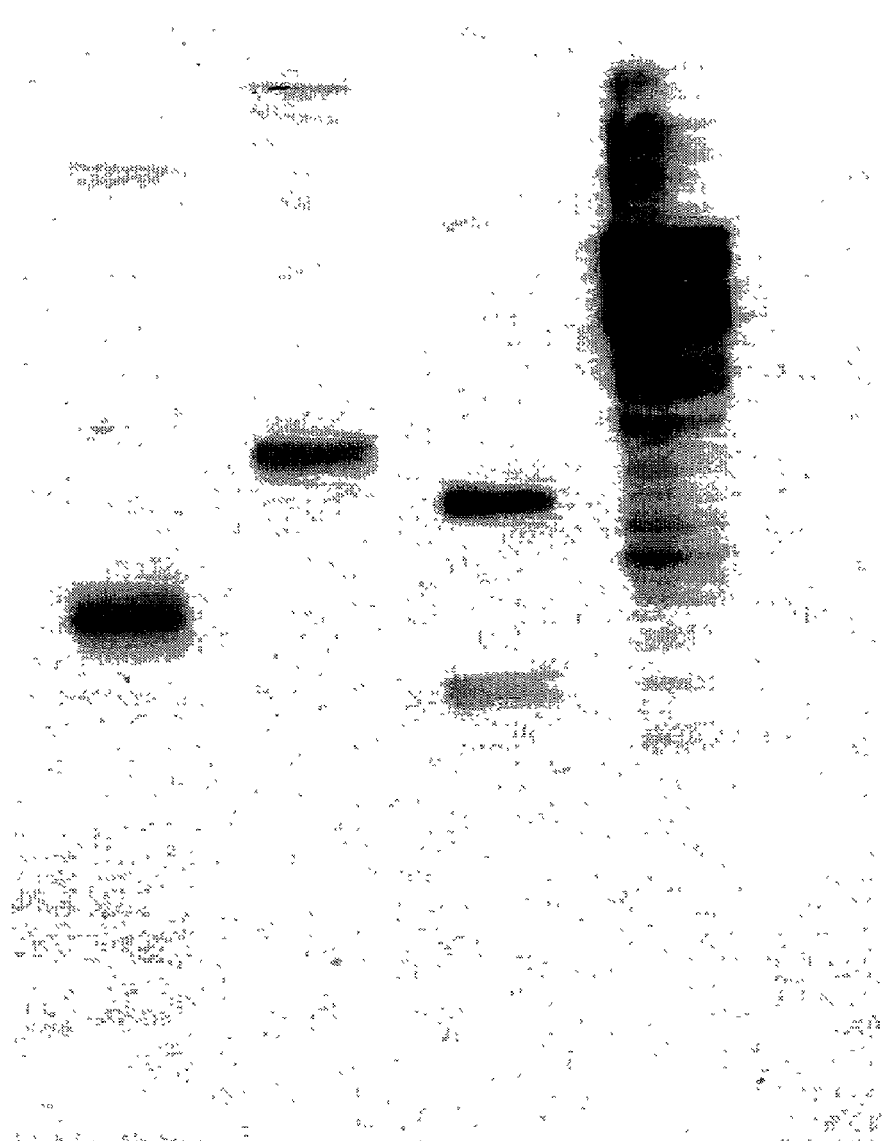
Figure 3:
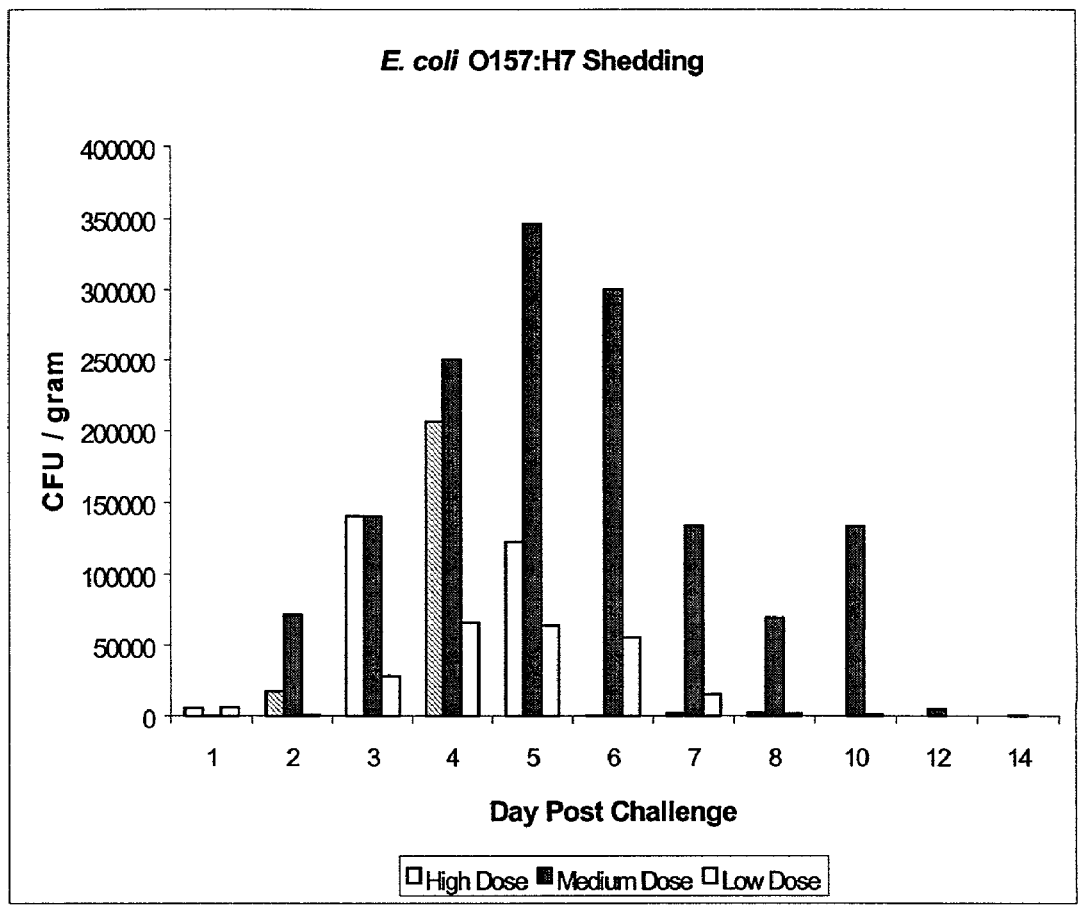
Figure 4:
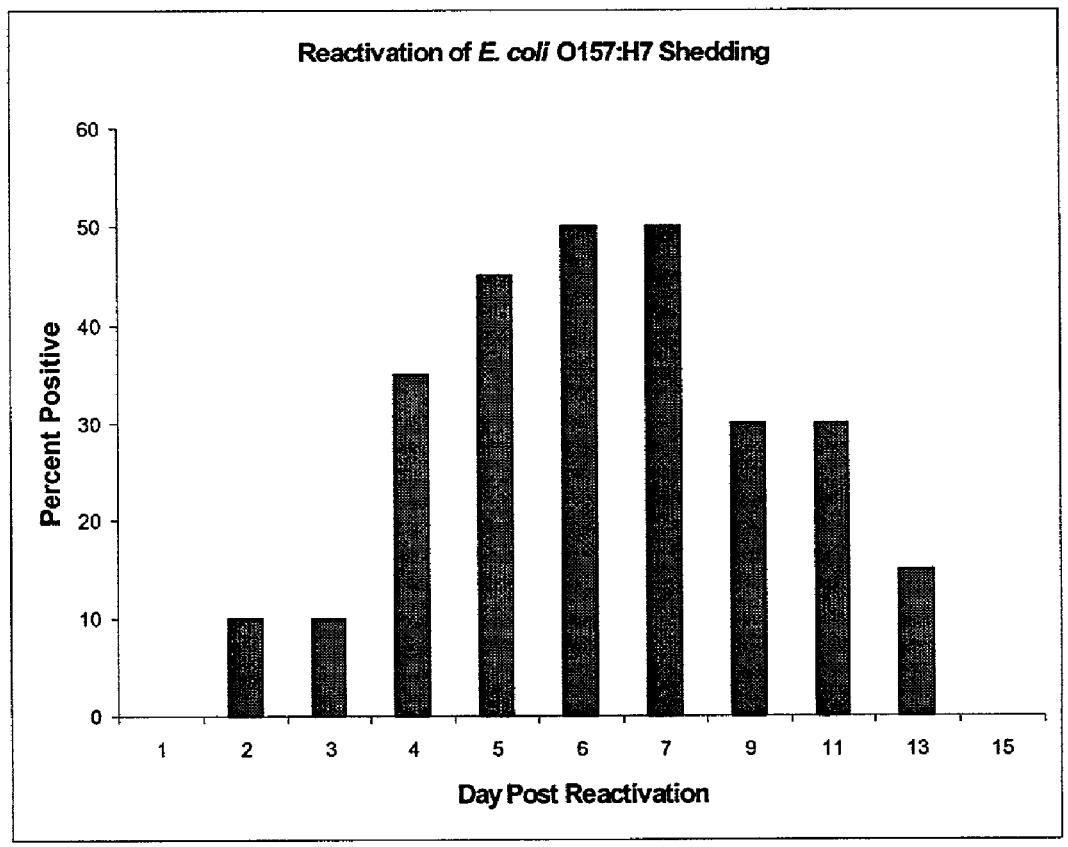

The purity of the recombinant proteins was assessed by SDS-PAGE on 10% gels followed by Coomassie blue staining. Typical gel profiles of the chromatographically purified recombinant (r) proteins are shown in FIG. 2. rEspA (lane 2) rEspB (lane 3) and rIntimin (lane 4), were recovered in relatively pure form, but rTir (lane 5) was subject to some degradation.

EXAMPLE 3

Vaccine Formulation and Delivery

Vaccines were formulated by mixing CCS or rEspA+rTir in 2 ml of a carrier containing from 30 to 40% of an adjuvant. Vaccines were delivered subcutaneously. Animals were immunized on day 1 and again at a 3–4 week intervals (boost). Serum samples were obtained prior to the first immunization, at the time of each boost and at the end of the experiment.

The serological response to immunization was determined using an enzyme-linked immunosorbent assay (ELISA). One hundred µl of rEspA (0.16 µg/well), rTir (0.1 µg/well), rEspB (0.24 µg/well) and rIntimin (0.187 µg/well) were used to coat the wells in microtiter plates and the plates were incubated overnight at 4° C. The wells were washed 3×, blocked with 0.5% nonfat dried milk in phosphate-buffered saline. Serial dilutions of sera were added to each well and incubated for 2 h at 37° C. The wells were washed and blocked and 100 µl of peroxidase-conjugated rabbit anti-bovine immunoglobulin G antibodies (1:5000) were added to each well for 1 h at 37° C. The wells were washed and plates were read at a wavelength of 492 nm.

EXAMPLE 4

Experimental Animals

Cattle, between the ages of 8 and 12 months, were purchased from local ranchers. Fecal samples were obtained daily from each animal for 14 days. The number of EHEC O157:H7 in the fecal samples was determined by plating on Rainbow Agar. The plates were incubated at 37° C. for 2 days and black colonies were enumerated. Growth was scored from 0–5. Animals having a score of 0 (no EHEC O157:H7) were used in all experiments.

EXAMPLE 5

Animal Colonization Model

A model for EHEC O157:H7 colonization of cattle, wherein the infection was sustained for >2 months, was developed using a dose-titration protocol.

EHEC O157:H7 were grown as in Example 1. Twenty-four cattle were divided into 3 groups of 8 animals each. Group 1 received $10^{6}$, Group 2 $10^{8}$ and Group 3 $10^{10}$ CFU of EHEC O157:H7 by oral-gastric intubation in a volume of 50 ml on day 0.

To monitor shedding, fecal material was collected on days 1 through 14. The fecal material was weighed, suspended in sterile saline and inoculated into culture media. Culture density was determined as in Example 1.

As shown in FIG. 3, there was no significant difference between numbers of EHEC O157:H7 shed by Group 2 ($10^8$ CFU) and Group 3 ($10^{10}$ CFU) cattle. Group 2 cattle shed the most EHEC O157:H7 on each of the 14 days. The number of EHEC O157,.H7 shed by Group 2 cattle reached a maximum on day 6 and declined to zero by day 14.

Animals shedding EHEC O157:H7 (hereinafter, "positive") were kept an additional 40 days during which time the number of EHEC O157:H7 shed decreased to an undetectable level. The shedding of EHEC O157:H7 by previously positive animals (hereinafter, "carriers") was reactivated by withholding feed for 24 hours and vaccinating with commercially-available clostridial or *H. somnus* vaccines. As shown in FIG. 4, the number of carrier animals shedding EHEC O157:H7 reached a maximum of approximately 50% on days 6 and 7 post-reactivation and declined to zero by day 15.

As a dose of $10^8$ CFU produced a detectable number of shed EHEC O157:H7 during the 14 days post-infection (FIG. 3) and resulted in persistently infected animals (FIG. 4), this dose was used as the challenge dose in subsequent experiments.

EXAMPLE 6

Protective Capacity of CCS

To test the vaccine potential of secreted proteins, CCS was mixed with the oil-based adjuvant, VSA3 (U.S. Pat. No. 5,951,988, incorporated herein by reference in its entirety; S. van Drunen Littel-van den Hurk et al., *Vaccine* (1993) 11:25) such that each 2 ml dose contained 200 μg of CCS protein and 30% (v/v) of adjuvant (CCS vaccine). For the control group, sterile saline was mixed with VSA3, such that each 2 ml dose contained 0 μg of CCS protein and 30% (v/v) of adjuvant (saline vaccine).

Sixteen cattle were divided in 2 groups of eight animals each. Group 1 cattle received 2 ml of CCS vaccine subcutaneously (experimental) and Group 2 cattle received 2 ml saline vaccine subcutaneously (control) on days 1 and 22 (boost). Seroconversion was assayed by ELISA (Example 3), on days 1 (pre-immunization), 22 and 36. As shown in Table 1, at day 22, Group 1 animals showed specific antibody titers to EspA and Tir and, at day 36, these titers showed a significant increase. Group 2 animals showed no specific antibody titers at days 22 and 36. In particular, the group which received the EHEC vaccine showed a 13-fold increase in specific antibody titer to type III secreted proteins after a single immunization and following the first booster, the eight animals in the EHEC vaccine group demonstrated a 45-fold increase in specific antibody titer while only one of the placebo vaccine group seroconverted ($X^2$, p=0.0002).

TABLE 1

Serological response to immunization with CCS

Specific Antibody Titers*-Group Means

| Group | Pre-immunization (Day 1) | Boost (Day 22) | Challenge (Day 36) |
|---|---|---|---|
| 1. Experimental | 350 | 5,000 | 12,500 |
| 2. Control | 450 | 500 | 650 |

*Values are group means expressed as the reciprocal of the highest dilution yielding a positive result.

Figure 7:
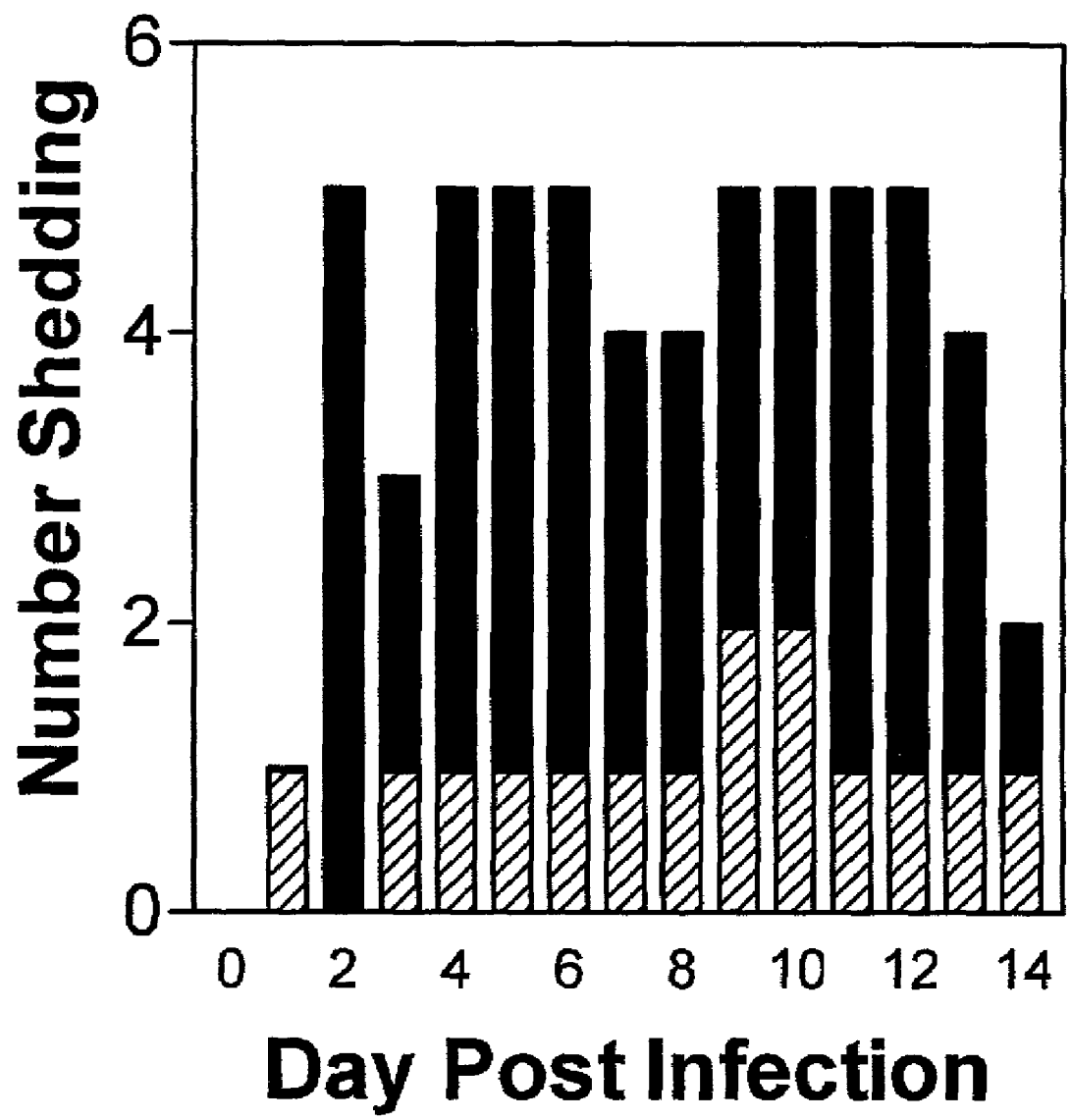

At day 36, Group 1 and Group 2 animals were challenged with $10^8$ CFU of EHEC O157:H7 by oral-gastric intubation and fecal shedding was monitored for 14 days (Example 5). As summarized in Table 2, fewer experimental animals shed EHEC O157:H7 than control animals and experimental animals that did shed, shed EHEC O157:H7 for a shorter period of time than control animals (FIG. 7). In particular, The median number of days during which the organism was shed in the vaccinated animals was 1.5 compared to 3.5 in the placebo group (Wilcoxin Signed Rank Test, p=0.08). Seven out of eight placebo-immunized animals shed the bacteria during the trial and four of those animals shed the bacteria for four or more consecutive days, indicating that they were persistently infected. Five out of eight EHEC vaccine-immunized animals shed bacteria at some point during the trial but only one animal shed the organism for more than two consecutive days, indicating that colonization was transient and significantly less than the placebo group. The total number of bacteria isolated from fecal samples was significantly lower among the EHEC-vaccinated group as compared to the placebo group (Wilcoxin Signed Rank Test, p=0.05), with the former having a median of 6.25 colony forming units (CFU) per gram of feces recovered compared to a median value of 81.25 CFU/g for the latter. Thus, vaccination with the type III-secreted proteins appeared to reduce the ability of the organism to colonize the intestine as reflected by the decrease in the number of days animals shed the organism as well as the numbers of shed bacteria detected by fecal culture.

TABLE 2

Shedding by experimental and control animals

|  | Experimental | Control |
|---|---|---|
| Animals shedding >1 day | 1/8 | 6/8 |
| Number of days with scores of >1 | 1 | 8 |
| Average days of shedding per animal | 0.875 | 2.5 |
| Total days shedding per group | 7 | 20 |

These data show that CCS induced an antibody response in cattle that reduced both number of animals shedding EHEC O157:H7 and the number of days during which EHEC O157:H7 were shed.

In order to enhance the effectiveness of the vaccine formulation, groups of 6 calves were immunized as described above with one of three doses of secreted proteins (50 μg, 100 μg, 200 μg) or a placebo and the serological response was measured in serum samples taken at days 0, 21 (boost) and 35. No significant difference in anti-EHEC, anti-Tir or anti-EspA responses were observed between any of the groups which received the EHEC vaccine at any time point but all three were significantly higher than the placebo group on days 21 and 35. Thus, a second vaccine trial was designed in which three groups of yearling cattle were immunized three times with 50 μg of secreted proteins (n=13), 50 μg of secreted proteins from a tir mutant (ΔTir, n=10) or a placebo (n=25). The adjuvant used was VSA3 and animals were immunized by subcutaneous injection on days 0, 21, and 35, followed by oral challenge with $E. coli$ O157:H7 on day 49. The serological response to immunization is shown in Table 3 (days 0 and 49 only) and was comparable to that observed in the trial described above. The group which received the ΔTir vaccine showed a response of similar magnitude against total secreted proteins as the group which received the vaccine prepared from the wild-type strain, but, as expected, a significantly reduced response to Tir (Wilcoxin Signed Rank Test, p=0.006). However, the former group did show an increase in anti-Tir antibody levels (Wilcoxin Signed Rank Test, p=0.009), indicating either exposure to an organism producing an immunologically related molecule or natural exposure to $E. coli$ O157:H7. This is further supported by the observation that there was a significant increase in the anti-Tir antibody titer in the placebo group on the day of challenge (Wilcoxin Signed Rank Test, p=0.002) but no difference between the placebo or ΔTir groups (p=0.37, Kruskal-Wallis ANOVA). The response to EspA was similar in both the EHEC and ΔTir vaccine groups (p=0.45, Kruskal-Wallis ANOVA) and was significantly higher than the placebo-immunized animals (p<0.0001).

TABLE 3

Median serological response to immunization with secreted proteins prepared from wild-type $E. coli$ O157:H7 (EHEC), an isogenic tir mutant (ΔTir) or a placebo. Titers are expressed as geometric mean values of the last positive dilution of sera ( ). Numbers in parentheses represent the 25th–75th percentile.

|  |  | Anti-EHEC | | Anti-Tir | | Anti-EspA | |
|---|---|---|---|---|---|---|---|
| Group | n | Day 0 | Day 49 | Day 0 | Day 49 | Day 0 | Day 49 |
| EHEC | 13 | 10 (10–100) | 6400 (3200–12800) | 100 (10–200) | 1600 (800–3200) | 100 (10–200) | 400 (200–1600) |

TABLE 3-continued

Median serological response to immunization with secreted proteins prepared from wild-type E. coli O157:H7 (EHEC), an isogenic tir mutant (ΔTir) or a placebo. Titers are expressed as geometric mean values of the last positive dilution of sera ( ). Numbers in parentheses represent the 25th–75th percentile.

| Group | n | Anti-EHEC | | Anti-Tir | | Anti-EspA | |
|---|---|---|---|---|---|---|---|
| | | Day 0 | Day 49 | Day 0 | Day 49 | Day 0 | Day 49 |
| ΔTir | 10 | 10 (10–100) | 6400 (3200–25600) | 10 (10–200) | 200 (100–800) | 100 (10–200) | 300 (100–1600) |
| Placebo | 25 | 10 (10–200) | 10 (10–200) | 100 (10–200) | 200 (10–400) | 100 (10–200) | 100 (10–200) |

Figure 8:
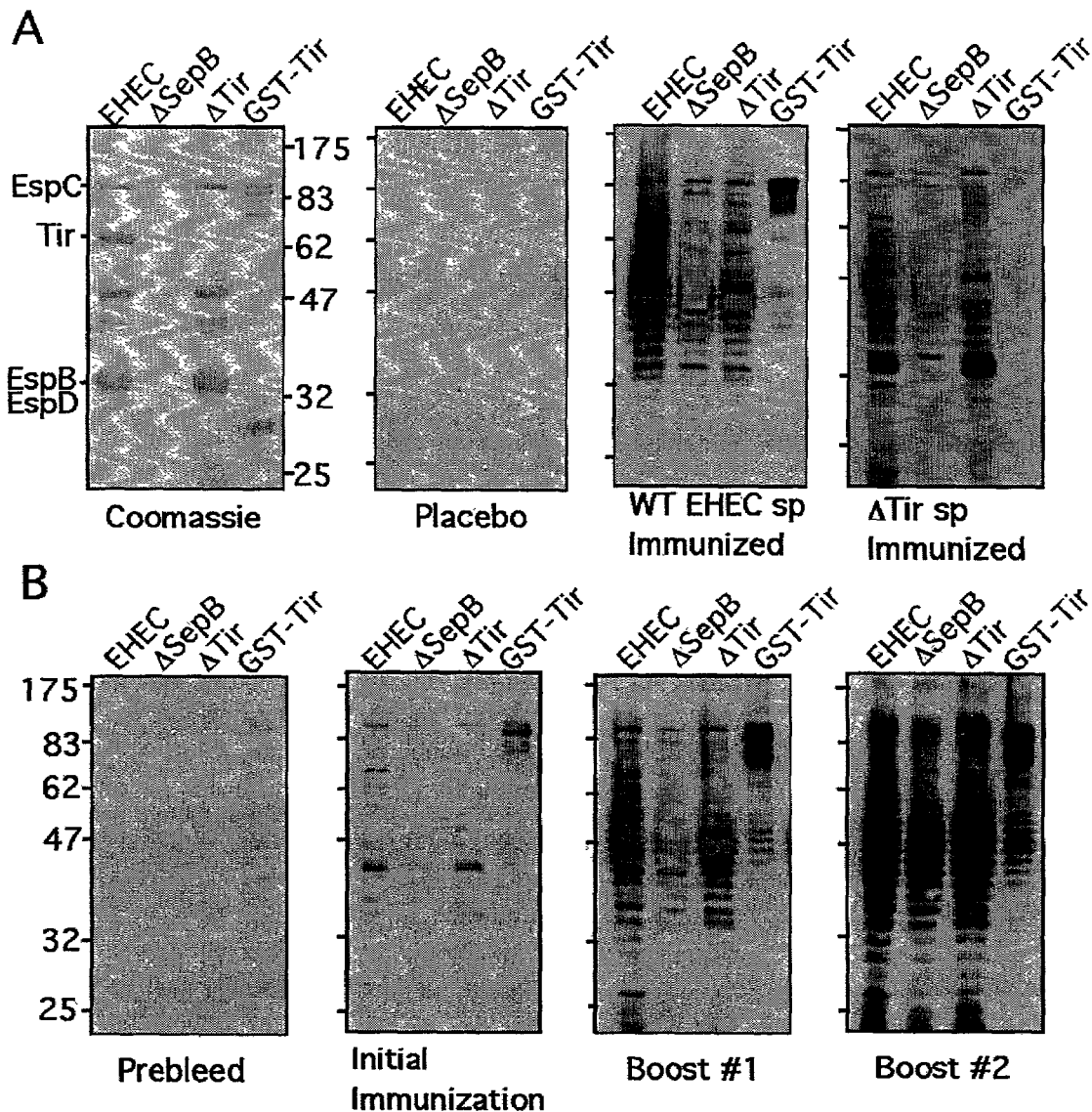

The immune response against each vaccine formulation was also analyzed qualitatively by Western blotting using sera from two representative animals per group. The results for representative animals are shown in FIG. 8 and demonstrate that the proteins secreted by the type III system were highly immunogenic in cattle. The response in the EHEC and ΔTir vaccine groups was similar with the exception of the response against Tir which was absent in the latter group (FIG. 8, top panels). EspB, EspD and Tir were all reactive, and following the second immunization on day 21 a significant response against lipopolysaccharide was also observed. The kinetics of the immune response in a vaccinated animal (FIG. 8, bottom panels) show that anti-Tir antibodies were detectable following a single immunization, as were antibodies against 43-kDa and 100-kDa proteins. The latter proteins were produced by the wild-type strain as well as the sepB and tir mutants and the 100 kDa protein is probably EspP, a non-type III EHEC secreted protein.

Following oral challenge with E. coli O157:H7 on day 49, each group was monitored daily for fecal shedding of the organism for 14 days. In this experiment, bacteria were cultured following immunomagnetic enrichment (J. Van Donkersgoed et al., Can. Vet. J. (2001) 42:714, Chapman and Siddons, J. Med. Microbiol. (1996) 44:267) rather than direct plating since yearling cattle shed less than calves in this infection model. On the day of challenge, two animals in the placebo group were culture-positive for E. coli O157:H7 and were eliminated from the trial. The placebo-immunized animals shed the organism after challenge much more than those in the two EHEC vaccine groups (FIG. 9). Those which received the placebo vaccine shed the organism for a median of 4 days, significantly longer than the median of 0 days by the other two vaccine groups (p=0.0002, Kruskal-Wallis ANOVA). Significantly fewer bacteria were recovered from the EHEC and ΔTir vaccine groups (p=0.04, Kruskal-Wallis ANOVA). From day 2 post-infection onwards, 78% of the placebo animals shed the organism for at least one day as compared to 15% of the EHEC and 30% of the ΔTir vaccinates (Table 4).

The data presented above demonstrate that virulence factors of EHEC, namely those secreted by the type III system, can be used as effective vaccine components for the reduction of colonization of cattle by EHEC bacteria, such as EHEC O157:H7. These proteins are major targets of the immune response in humans following infection (Li et al., Infect. Immun. (2000) 68:5090), although cattle do not usually mount a significant serological response against these proteins following natural exposure to the organism. However, animals vaccinated with these proteins are primed and show an increase in anti-EHEC and anti-Tir titers following oral challenge with the organism.

Tir is likely required for colonization of the bovine intestine, and this is supported by the observation that a vaccine containing secreted proteins from a ΔTir E. coli O157:H7 strain was not as efficacious as an identical formulation from an isogenic wild-type isolate. However, the former vaccine was significantly more efficacious than a placebo suggesting that immunity against colonization is multifactorial in nature. This is supported by the Western blot analysis of the response to immunization in which several protein components as well as lipopolysaccharide were recognized. The contribution to protection by lipopolysaccharide is not known, but the presence of antibodies against this molecule does not correlate with protection in a murine EHEC model (Conlan et al., Can. J. Microbiol. (1999) 45:279; Conlan et al., Can. J. Microbiol. (2000) 46:283). Also, immunization with recombinant Tir and EspA can reduce numbers of bacteria shed, but not the actual numbers of animals nor the duration of shedding.

The prevalence of non-O157 serotypes in North America appears to be increasing and represents a significant portion of EHEC infections in other geographical locations. Since the type III-secreted antigens appear to be relatively conserved among non-O157 EHEC serotypes, this vaccine formulation is likely broadly cross-protective, in contrast to formulations based upon the O157 LPS antigen.

TABLE 4

Number of animals shedding E. coli O157:H7 at any time between day 2 and day 14 post-challenge.

| Vaccine | Number Shedding | n | Percent Shedding | p-value |
|---|---|---|---|---|
| EHEC | 2 | 13 | 15.4 | 0.003 |
| ΔTir | 3 | 10 | 30 | 0.008 |
| Placebo | 18 | 23 | 78.3 | 1 |

EXAMPLE 7

Protective Capacity of rEspA+rTir and rEspB+rIntimin rEspA, rTir, rEspB and rIntimin were mixed with the oil-based adjuvant, VSA3, such that each 2 ml dose contained 50 μg of rEspA+rTir or of rEspB+rIntimin and 30% (v/v) of adjuvant. Sterile saline was mixed with VSA3, such that each 2 ml dose contained 0 μg of rEspA+rTir or of rEspB+rIntimin and 30% (v/v) of adjuvant.

Thirty four cattle were divided in 4 groups. Ten cattle, Group 1, were immunized with rEspA+rTir vaccine (experimental) and 10 cattle, Group 2, were immunized with rEspB+rIntimin vaccine (experimental) on days 1, 22

Figure 5:
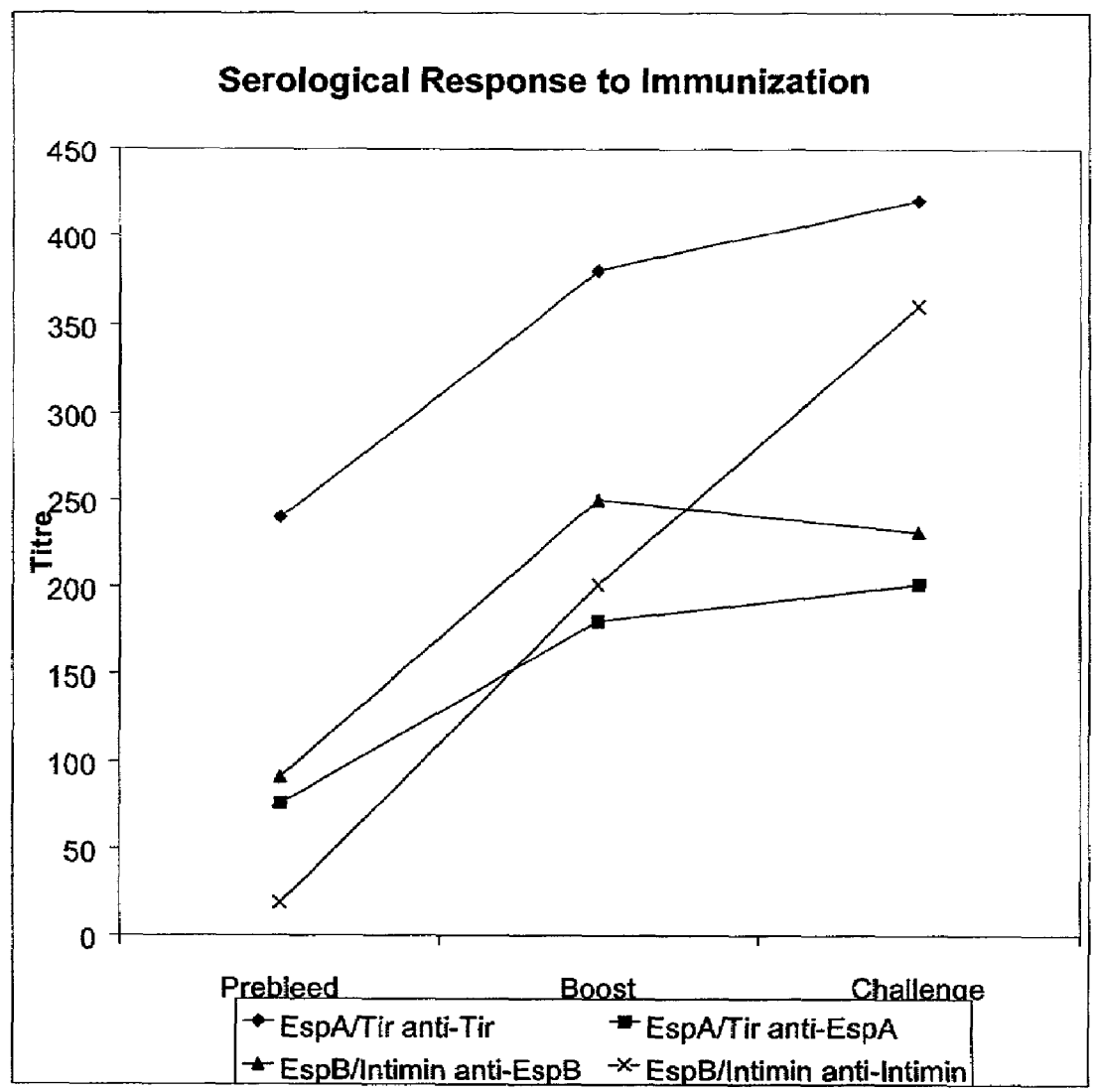

(boost) and 36. Seven cattle, Group 3, and 7 cattle, Group 4, were immunized with saline vaccine (control) an days 1, 22 (boost) and 36. Seroconversion was assayed by ELISA (Example 3) on days 1 (pre-immunization), 22 and 36. As shown in FIG. 5, at day 22, Group 1 animals showed specific antibody titers to rEspA and to rTir and Group 2 animals showed specific antibody titers to rEspB and to rIntimin. Also, as shown in FIG. 5, at day 36, Group 1 animals showed an increase in specific antibody titer to rTir and no change in specific antibody titer to rEspA and Group 2 animals showed an increase in specific antibody titer to rIntimin and a decrease in specific antibody titer to rEspB. Groups 3 and 4 animals showed no specific antibody titers at days 22 and 36.

Figure 6:
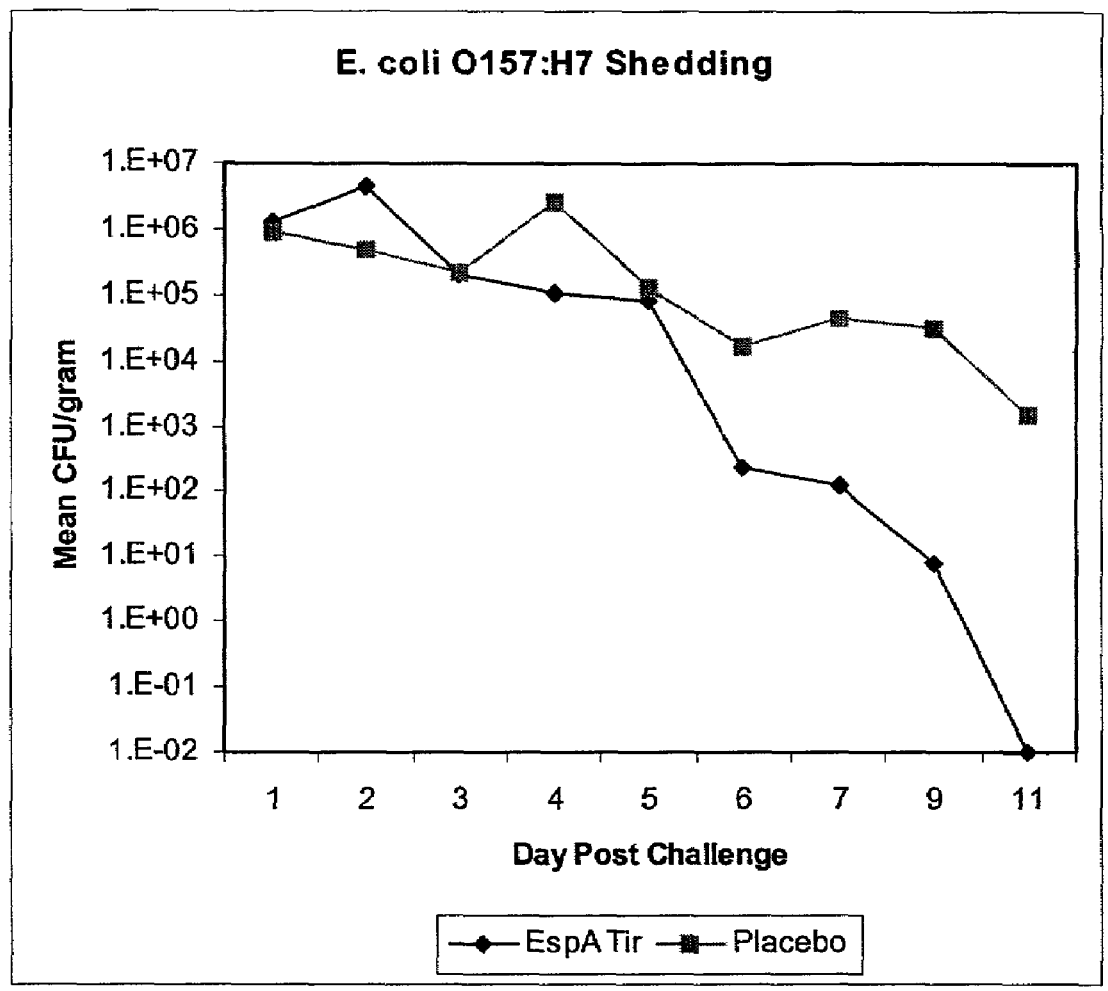

At day 36, Groups 1–4 animals were challenged with $10^8$ CFU of EHEC O157:H7 and shedding was monitored daily for 14 days (Example 5). As shown in FIG. 6, differences in shedding between Group 1 (rTir+rEspA) animals and Group 3 (saline) animals was minimal during the first 5 days post-challenge. However, during the second week post-challenge differences in Group 1 animals and Group 3 animals were evident. Fewer Group 1 animals shed EHEC O157:H7 than Group 3 animals. Group 1 animals shed less EHEC O157:H7 in their feces for shorter time periods than Group 3 animals. Differences in shedding between Group 2 (rEspB+rIntimin) and Group 4 (saline) animals were not evident with respect to the number of animals shedding, the number of EHEC O157:H7 shed and the time period of shedding.

These data show that the antibody response induced by rEspA+rTir vaccine interfered with EHEC O157:H7 colonization of cattle, whereas the antibody response induced by rEspB+rIntimin vaccine did not interfere with EHEC O157:H7 colonization of cattle.

EXAMPLE 8

Protective Capacity of CCS+rEspA+rTir

CCS, CCS+rEspA, CCS+rTir, CCS+rEspA+rTir and saline are mixed with an adjuvant.

Twenty-five cattle are divided into 5 groups of five 5 cattle and are immunized an days 1 and 22 (boost). Group 1 receives CCS vaccine, Group 2 CCS+rEspA vaccine, Group 3 CCS+rTir vaccine, Group 4 CCS+rEspA+rTir vaccine, and Group 5 saline vaccine. Seroconversion is assayed by ELISA (Example 3) on days 1 (pre-immunization), 22 (boost) and 36. On days 22 and 36 each of Groups 1–5 animals show specific antibody titers against EspA and Tir, whereas Group 6 animals show no specific antibody titers.

At day 36, Groups 1–5 animals are challenged with $10^8$ CFU of EHEC O157:H7 and shedding is monitored daily for 14 days (Example 5). Fewer animals in Groups 1–4 shed EHEC O157:H7 than animals in Group 5. Group 5 animals shed the most EHEC O157:H7; Group 1 animals shed less EHEC O157:H7 than Group 5 animals and Groups 2–4 animals shed less EHEC O157:H7 than Group 1 animals.

EXAMPLE 9

Protective Capacity of CCS with Various Antigens

CSS is mixed with and adjuvant, such that each 2 ml dose contains 0, 50, 100 or 200 µg of CCS and 30% (v/v) of adjuvant (Table 5).

TABLE 5

Protective capacity of CCS with various adjuvants

| Antigen | Group | μg | Adjuvant |
|---|---|---|---|
| CCS | 1 | 50 | Emulsigen-Plus |
| CCS | 2 | 100 | Emulsigen-Plus |
| CCS | 3 | 200 | Emulsigen-Plus |
| CCS | 4 | 200 | Carbigen |
| CCS | 5 | 100 | MCC |
| CCS | 6 | 200 | MCC |
| CCS | 7 | 200 | MCC + Carbigen |
| CCS | 8 | 200 | VSA |
| CCS | 9 | 0 (control) | Emulsigen-Plus |

Seventy-two cattle are divided in 9 groups of 8 cattle. Groups 1–8 animals are immunized with CCS+adjuvant (Table 5) and Group 9 cattle are immunized with saline+adjuvants on days 1 and 22 (boost). Seroconversion is assayed by ELISA (Example 3) on days 1 (pre-immunization), 22 (boost) and 36. Groups 1–8 (CCS+adjuvant) animals show specific antibody titers to EspA and Tir on days 22 and 36. Group 9 (saline+adjuvant) animals show no specific antibody titers on days 22 and 36.

EXAMPLE 10

Protective Capacity of CCS in Dairy Cows

Twenty adult dairy cows are divided in 2 groups of 10 cows. Group 1 is immunized with CCS vaccine and Group 2 is immunized with saline-vaccine on days 1 and day 22 (boost). Seroconversion is assayed by ELISA (Example 3) on days 1 (pre-immunization), 22 and 36. On days 22 and 36 Group 1 cows show specific antibody titers against EspA and Tir, whereas Group 2 cows show no specific antibody titers.

At day 36, Groups 1 and 2 cows are challenged with $10^8$ CFU of EHEC O157:H7 and shedding is monitored daily for 14 days (Example 5). Fewer Group 1 cows shed EHEC O157:H7 than Groups 2 cows. Group 1 cows shed less EHEC O157:H7 for a shorter period of time than Groups 2 cows.

Six months after the initial immunization, Group 1 and 2 cows are again immunized (2nd boost) via the subcutaneous route. On day 14 following the 2nd boost, antibody titers are assayed by ELISA (Example 3). Group 1 cows have specific antibody titers to EspA and Tir, whereas Group 2 cows have no specific antibody titers.

On day 14 following the 2nd boost, Groups 1 and 2 cows are again challenged with $10^8$ CFU of EHEC O157:H7 and shedding is monitored daily for 14 days (Example 5). Fewer Group 1 (CCS) cows shed EHEC O157:H7 than Group 2 (saline) cows. Group 1 cows shed less EHEC O157:H7 for a shorter time periods than Group 2 cows.

EXAMPLE 11

Protective Capacity of CCS in Calves

Ten weaned calves (3–6 month old) are divided into 2 groups of 5 calves and are immunized prior to entry into a feed-lot (day 0) and on the day of entry into a feed lot (day 1, boost). Group 1 calves receive CCS vaccine and Group 2 calves receive saline vaccine. Seroconversion is assayed by ELISA (Example 3) on days 0, 1 and 14. On days 1 and 14

Group 1 (CCS) calves show specific antibody titers to EspA and Tir, whereas Group 2 (saline) calves show no specific antibody titers.

At day 14, Groups 1 and 2 calves are challenged with $10^8$ CFU of EHEC O157:H7 and shedding is assayed daily for 14 days (Example 5). Fewer Group 1 calves shed EHEC O157:H7 than Group 2 calves. Group 1 calves shed less EHEC O157:H7 for a shorter time period than Group 2 calves.

Ten weaned calves (3–6 month old) we divided into 2 groups of 5 calves and are immunized on the day of entry into a feed-lot (day 1) and on day 22 (boost) in the feed lot. Group 1 calves receive CCS vaccine and Group 2 calves receive saline vaccine. Seroconversion is assayed by ELISA (Example 3) on days 1 (pre-immunization), 22 and 36. On days 22 and 36 Group 1 (CCS) calves show specific antibody titers to EspA and Tir, whereas Group 2 (saline) calves show no specific antibody titers.

At day 36, Groups 1 and 2 calves are challenged with $10^8$ CFU of EHEC O157:H7 and shedding is assayed daily for 14 days (Example 5). Fewer Group 1 calves shed EHEC O157:H7 than Group 2 calves. Group 1 calves shed less EHEC O157:H7 for a shorter time period than Group 2 calves.

EXAMPLE 12

Protective Capacity of CCS in Sheep

Twenty adult sheep are divided in 2 groups of 10 sheep. Group 1 is immunized with CCS vaccine and Group 2 is immunized with saline vaccine on day 1 and day 22 (boost). Seroconversion is assayed by ELISA (Example 3) on days 1 (pre-immunization), 22 and 36. On days 22 and 36 Group 1 sheep show specific antibody titers against EspA and Tir, whereas Group 2 sheep show no specific antibody titers.

At day 36, Groups 1 and 2 sheep are challenged with $10^8$ CFU of EHEC O157:H7 and shedding is monitored daily for 14 days (Example 5). Fewer Group 1 sheep shed EHEC O157:H7 than Group 2 sheep. Group 1 sheep shed less EHEC O157:H7 for a shorter period of time than Group 2 sheep.

Thus, compositions and methods for treating and preventing enterohemorragic *E. coli* colonization of mammals have been disclosed. Although preferred embodiments of the subject invention have been described in some detail, it is understood that obvious variations can be made without departing from the spirit and the scope of the invention as defined by the appended claims.

We claim:

1. A method for reducing colonization of enterohemorrhagic *Escherichia coli* (EHEC) in a non-human mammal comprising administering to said non-human mammal an effective amount of a composition comprising an isolated EHEC cell culture supernatant, wherein the cell culture supernatant is produced by the process of incubating the cell culture in media comprising minimal media supplemented with 0.1% Casamino Acids, 0.4% glucose, 8 mM $MgSO_4$ and 44 mM $NaHCO_3$.

2. A method for reducing shedding of enterohemorrhagic *Escherichia coli* (EHEC) from a non-human mammal comprising administering to said non-human mammal an effective amount of a composition comprising an isolated EHEC cell culture supernatant, wherein the cell culture supernatant is produced by the process of incubating the cell culture in media comprising minimal media supplemented with 0.1% Casamino Acids, 0.4% glucose, 8 mM $MgSO_4$ and 44 mM $NaHCO_3$.

3. The method of claim 1, wherein the non-human mammal is a ruminant.

4. The method of claim 3, wherein the ruminant is a bovine subject.

5. The method of claim 1, wherein the composition further comprises an immunological adjuvant.

6. The method of claim 1, wherein the EHEC is EHEC O157:H7.

7. The method of claim 1, wherein the EHEC is EHEC O157:NM.

8. The method of claim 5, wherein the immunological adjuvant comprises an oil-in-water emulsion.

9. The method of claim 5, wherein the immunological adjuvant comprises a mineral oil and dimethyldioctadecylammonium bromide.

10. The method of claim 5, wherein the immunological adjuvant comprises a non-oil-in-water emulsion.

11. The method of claim 5, wherein the immunological adjuvant is present in the composition at a concentration of 20% to 40% (v/v).

12. The method of claim 11, wherein the immunological adjuvant is present in the composition at a concentration of 30% (v/v).

13. The method of claim 1, wherein the composition further comprises one or more recombinant or purified EHEC antigens selected from the group consisting of EspA, EspB, EspD, Tir and Intimin.

14. The method of claim 13, wherein EspA+Tir comprise 10% to 50% of EHEC protein in the cell culture supernatant present in the composition.

15. The method of claim 5, wherein the composition further comprises one or more recombinant or purified EHEC antigens selected from the group consisting of EspA, EspB, EspD, Tir and Intimin.

16. The method of claim 15, wherein EspA+Tir comprise 10% to 50% of EHEC protein in the cell culture supernatant present in the composition.

17. The method of claim 2, wherein the non-human mammal is a ruminant.

18. The method of claim 17, wherein the ruminant is a bovine subject.

19. The method of claim 2, wherein the composition further comprises an immunological adjuvant.

20. The method of claim 2, wherein the EHEC is EHEC O157:H7.

21. The method of claim 2, wherein the EHEC is EHEC O157:NM.

22. The method of claim 19, wherein the immunological adjuvant comprises an oil-in-water emulsion.

23. The method of claim 19, wherein the immunological adjuvant comprises a mineral oil and dimethyldioctadecylammonium bromide.

24. The method of claim 19, wherein the immunological adjuvant comprises a non-oil-in-water emulsion.

25. The method of claim 19, wherein the immunological adjuvant is present in the composition at a concentration of 20% to 40% (v/v).

26. The method of claim 19, wherein the immunological adjuvant is present in the composition at a concentration of 30% (v/v).

27. The method of claim 2, wherein the composition further comprises one or more recombinant or purified EHEC antigens selected from the group consisting of EspA, EspB, EspD, Tir and Intimin.

28. The method of claim 27, wherein EspA+Tir comprise 10% to 50% of EHEC protein in the cell culture supernatant present in the composition.

29. The method of claim 19, wherein the composition further comprises one or more recombinant or purified EHEC antigens selected from the group consisting of EspA, EspB, EspD, Tir and Intimin.

30. The method of claim 29, wherein EspA+Tir comprise 10% to 50% of EHEC protein in the cell culture supernatant present in the composition.

31. The method of claim 5 or 19, wherein the immunological adjuvant comprises an agent selected from the group consisting of an emulsifying agent, a muramyl dipeptide, an aqueous agent, a chitosan-based agent, a saponin, an oil, a lipopolysaccharide, a bacterial cell wall extract, a bacterial DNA, a bacterial complex, a synthetic oligonucleotide, and a aliphatic nitrogenous base.

32. The method of claim 31, wherein the emulsifying agent is selected from the group consisting of a natural emulsifying agent, a synthetic emulsifying agent, an anionic emulsifying agent, a cationic emulsifying agent, and a nonionic agent.

33. The method of claim 32, wherein the natural emulsifying agent is selected from the group consisting of acacia, gelatin, lecithin, and cholesterol.

34. The method of claim 32, wherein the anionic emulsifying agent is selected from the group consisting of a potassium salt of lauric acid, a potassium salt of oleic acid, a sodium salt of lauric acid, a sodium salt of oleic acid, an ammonium salt of lauric acid, an ammonium salt of oleic acid, a calcium salt of a fatty acid, a magnesium salt of a fatty acid, an aluminum salt of a fatty acid, a metallic soap, and an organic sulfonate.

35. The method of claim 34, wherein the organic sulfonate is sodium lauryl sulfate.

36. The method of claim 32, wherein the cationic emulsifying agent is ceryltrimethylammonium bromide.

37. The method of claim 32, wherein the synthetic agent is selected from the group consisting of a glyceryl ester, a polyoxyethylene glycol ester, a polyoxyethylene glycol ether, and a sorbitan fatty acid ester.

38. The method of claim 37, wherein the glyceryl ester is glyceryl monostearate.

39. The method of claim 37, wherein the sorbitan fatty acid ester is selected from the group consisting of a sorbitan monopalmitate and polyoxyethylene derivatives thereof.

40. The method of claim 37, wherein the polyoxyethylene derivatives is polyoxyethylene sorbitan monopalmitate.

41. The method of claim 31, wherein the aqueous agent is aluminum hydroxide.

42. The method of claim 31, wherein the oil is selected from the group consisting of a mineral oil, a vegetable oil, and an animal oil.

43. The method of claim 42, wherein the vegetable oil is selected from the group consisting of canola oil, almond oil, cottonseed oil, corn oil, olive oil, peanut oil, safflower oil, sesame oil, and soybean oil.

44. The method of claim 42, wherein the animal oil is selected from the group consisting of cod liver oil, halibut oil, menhaden oil, orange roughy oil and shark liver oil.

45. The method of claim 5 or 19, wherein the immunological adjuvant comprises an oil component.

46. The method of claim 45, wherein the oil component is selected from the group consisting of a single oil, and a mixture of oils.

47. The method of claim 5 or 19, wherein the immunological adjuvant comprises Mycobacterial cell wall extract.

48. The method of claim 5 or 19, wherein the immunological adjuvant comprises Mycobacterial DNA.

49. The method of claim 5 or 19, wherein the immunological adjuvant comprises a Mycobacterial cell wall complex.

50. The method of claim 31, wherein the aliphatic nitrogenous base is selected from the group consisting of an amine, a quaternary ammonium compound, a guanidine, a benzamidine, and a thiouronium.

51. The method of claim 5 or 19, wherein the immunological adjuvant comprises dimethyl-dioctadecylammonium bromide.

52. The method of claim 31, wherein the aliphatic nitrogenous base is N,N-dioctadecyl-N,N-bis(2-hydroxyethyl) propanediamine.

53. The method of claim 14, 16, 18, or 30, wherein EspA+Tir comprise 20% EHEC protein in the culture supernatant present in the composition.

54. The method of claim 3 or 17, wherein the ruminant is an ovine subject.

55. The method of claim 19, wherein the immunological adjuvant comprises an agent selected from the group consisting of an emulsifying agent, a muramyl dipeptide, an aqueous agent, a chitosan-based agent, a saponin, an oil, a lipopolysaccharide, a bacterial cell wall extract, a bacterial DNA, a bacterial complex, a synthetic oligonucleotide, and a aliphatic nitrogenous base.

56. The method of claim 19, wherein the immunological adjuvant comprises an oil component.

57. The method of claim 24, wherein the non-oil-in-water emulsion is selected from the group consisting of an oil emulsion, a water-in-oil emulsion, and a water-in-oil-in-water emulsion.

58. The method of claim 19, wherein the immunological adjuvant comprises Mycobacterial cell wall extract.

59. The method of claim 19, wherein the immunological adjuvant comprises Mycobacterial DNA.

60. The method of claim 19, wherein the immunological adjuvant comprises a Mycobacterial cell wall complex.

61. The method of claim 19, wherein the immunological adjuvant comprises Mycobacterial cell wall extract.

62. The method of claim 19, wherein the immunological adjuvant comprises Mycobacterial DNA.

63. The method of claim 19, wherein the immunological adjuvant comprises a Mycobacterial cell wall complex.

64. The method of claim 19, wherein the immunological adjuvant comprises dimethyl-dioctadecylammonium bromide.

65. The method of claim 16, wherein EspA+Tir comprise 20% of EHEC protein in the cell culture supernatant present in the composition.

66. The method of claim 28, wherein EspA+Tir comprise 20% of EHEC protein in the cell culture supernatant present in the composition.

67. The method of claim 30, wherein EspA+Tir comprise 20% of EHEC protein in the cell culture supernatant present in the composition.

68. The method of claim 17, wherein the ruminant is an ovine subject.

69. The method of claim 1, wherein the cell culture supernatant is concentrated.

70. The method of claim 2, wherein the cell culture supernatant is concentrated.

71. A method for reducing colonization of enterohemorrhagic *Escherichia coli* (EHEC) in a non-human mammal comprising administering to said non-human mammal an effective amount of a composition comprising an isolated EHEC cell culture supernatant containing one or more EHEC serotypes wherein the cell culture supernatant is produced by the process of incubating the cell culture in media comprising minimal media supplemented with 0.1% Casamino Acids, 0.4% glucose, 8 mM $MgSO_4$ and 44 mM $NaHCO_3$.

72. The method of claim 71, wherein the cell culture supernatant is concentrated.

73. The method of claim 71, wherein the one of more EHEC serotypes are selected from the group consisting of O157, O158, O5, O8, O18, O26, O45, O48, O52, O55, O75, O76, O78, O84, O91, O103, O104, O111, O113, O114, O116, O118, O119, O121, O125, O28, O145, O146, O163, and O165.

74. The method of claim 71, wherein the step of administering is by a route selected from the group consisting of oral, subcutaneous, intramuscular, intravenous, subcutaneous, intradermal, transdermal and subdermal.

75. A method for reducing shedding of enterohemorrhagic *Escherichia coli* (EHEC) from a non-human mammal comprising administering to said non-human mammal an effective amount of a composition comprising an isolated EHEC cell culture supernatant containing one or more EHEC serotypes wherein the cell culture supernatant is produced by the process of incubating the cell culture in media comprising minimal media supplemented with 0.1% Casamino Acids, 0.4% glucose, 8 mM $MgSO_4$ and 44 mM $NaHCO_3$.

76. The method of claim 75, wherein the cell culture supernatant is concentrated.

77. The method of claim 75, wherein the one of more EHEC serotypes are selected from the group consisting of O157, O158, O5, O8, O18, O26, O45, O48, O52, O55, O75, O76, O78, O84, O91, O103, O104, O111, O113, O114, O116, O118, O119, O121, O125, O28, O145, O146, O163, and O165.

78. The method of claim 75, wherein the step of administering is by a route selected from the group consisting of oral, subcutaneous, intramuscular, intravenous, subcutaneous, intradermal, transdermal and subdermal.

79. The method of claim 1, wherein the step of administering is by a route selected from the group consisting of oral, subcutaneous, intramuscular, intravenous, subcutaneous, intradermal, transdermal and subdermal.

80. The method of claim 2, wherein the step of administering is by a route selected from the group consisting of oral, subcutaneous, intramuscular, intravenous, subcutaneous, intradermal, transdermal and subdermal.

* * * * *

UNITED STATES PATENT AND TRADEMARK OFFICE
CERTIFICATE OF CORRECTION

| | | |
|---|---|---|
| PATENT NO. | : 7,300,659 B2 | Page 1 of 1 |
| APPLICATION NO. | : 10/039760 | |
| DATED | : November 27, 2007 | |
| INVENTOR(S) | : B. Brett Finlay and Andrew A. Potter | |

It is certified that error appears in the above-identified patent and that said Letters Patent is hereby corrected as shown below:

On the title page, item (56), line 2, FOREIGN PATENT DOCUMENTS should read:

WO 99/24576

Title page item (57), ABSTRACT, line 2, should read:

enterohemorrhagic

Column 1, FIELD OF THE INVENTION lines 3 and 5, should read:

enterohemorrhagic

Column 1, BACKGROUND OF THE INVENTION, line 1, should read:

Enterohemorrhagic

Signed and Sealed this

Eighth Day of July, 2008

JON W. DUDAS
*Director of the United States Patent and Trademark Office*